United States Patent
Hagihara et al.

(10) Patent No.: US 12,104,292 B2
(45) Date of Patent: Oct. 1, 2024

(54) FABRIC MATERIAL WITH ELECTRODE WIRING

(71) Applicant: LINTEC CORPORATION, Tokyo (JP)

(72) Inventors: Yoshiaki Hagihara, Tokyo (JP); Shigeto Okuji, Tokyo (JP)

(73) Assignee: LINTEC CORPORATION, Tokyo (JP)

( * ) Notice: Subject to any disclaimer, the term of this patent is extended or adjusted under 35 U.S.C. 154(b) by 280 days.

(21) Appl. No.: 17/286,588

(22) PCT Filed: Oct. 22, 2019

(86) PCT No.: PCT/JP2019/041420
§ 371 (c)(1),
(2) Date: Apr. 19, 2021

(87) PCT Pub. No.: WO2020/085345
PCT Pub. Date: Apr. 30, 2020

(65) Prior Publication Data
US 2021/0388543 A1    Dec. 16, 2021

(30) Foreign Application Priority Data
Oct. 23, 2018 (JP) ................................. 2018-199111

(51) Int. Cl.
*D03D 1/00* (2006.01)
*A41D 1/00* (2018.01)
(Continued)

(52) U.S. Cl.
CPC .......... *D03D 1/0088* (2013.01); *A41D 1/002* (2013.01); *A41D 31/185* (2019.02);
(Continued)

(58) Field of Classification Search
CPC .......... D10B 2401/061; D10B 2401/16; D10B 2401/18; D10B 2403/02431; D04B 1/123;
(Continued)

(56) References Cited

U.S. PATENT DOCUMENTS

| | | |
|---|---|---|
| 6,341,504 B1 * | 1/2002 | Istook .................... D04B 21/18 66/172 E |
| 2007/0080773 A1 | 4/2007 | Tang et al. |

(Continued)

FOREIGN PATENT DOCUMENTS

| | | | | |
|---|---|---|---|---|
| CN | 107385623 A | * | 11/2017 | ........... D03D 1/0088 |
| EP | 1506738 A1 | * | 2/2005 | ......... A41D 13/1281 |

(Continued)

OTHER PUBLICATIONS

Machine Translation KR20130141283 (Year: 2013).*
(Continued)

*Primary Examiner* — Jennifer A Steele
(74) *Attorney, Agent, or Firm* — Rimon P.C.

(57) ABSTRACT

A fabric material with an electrode wiring includes: a fabric material body with stretchability; a first electrode portion that is disposed on a surface or in the interior of the fabric material body, and that includes a conductive linear body; a first wiring portion that is disposed on the surface or in the interior of the fabric material body so as to be electrically connected to the first electrode portion, and that includes a conductive linear body; a second electrode portion that is disposed on the surface or in the interior of the fabric material body, and that includes a conductive linear body; and a second wiring portion that is disposed on the surface or in the interior of the fabric material body so as to be electrically connected to the second electrode portion, and that includes a conductive linear body. In the fabric material with an electrode wiring, a resistance value between the first (Continued)

electrode portion and the second electrode portion is varied by stretching the fabric material with an electrode wiring.

16 Claims, 23 Drawing Sheets

(51) Int. Cl.
  *A41D 31/18* (2019.01)
  *D03D 15/533* (2021.01)
  *D03D 15/56* (2021.01)
(52) U.S. Cl.
  CPC .......... *D03D 15/533* (2021.01); *D03D 15/56* (2021.01); *D10B 2401/061* (2013.01); *D10B 2401/16* (2013.01); *D10B 2401/18* (2013.01)
(58) Field of Classification Search
  CPC . D04B 1/18; D04B 1/14; D04B 21/00; D03D 1/0088; D03D 15/533; D03D 15/56; D03D 15/275; D03D 15/593; A41D 1/002; A41D 31/185; A61B 5/27; A61B 5/256; A61B 2562/0209; A61B 5/6804; A61B 5/1116; A61B 2562/046; A61B 2562/222; A61B 5/25
  See application file for complete search history.

(56) References Cited

U.S. PATENT DOCUMENTS

| | | | |
|---|---|---|---|
| 2008/0170982 A1 | 7/2008 | Zhang et al. | |
| 2010/0070008 A1* | 3/2010 | Parker | A61M 25/0009 607/116 |
| 2013/0263351 A1* | 10/2013 | Tao | D02G 3/441 174/128.1 |
| 2014/0343390 A1 | 11/2014 | Berzowska et al. | |
| 2015/0376821 A1* | 12/2015 | McMaster | D04B 1/12 66/202 |
| 2017/0036066 A1 | 2/2017 | Chahine | |
| 2017/0176167 A1* | 6/2017 | Keller | G01L 1/225 |
| 2017/0327377 A1 | 11/2017 | Zhang et al. | |
| 2018/0020936 A1 | 1/2018 | Kwon et al. | |
| 2021/0244332 A1* | 8/2021 | Hagihara | D03D 15/00 |

FOREIGN PATENT DOCUMENTS

| | | | | |
|---|---|---|---|---|
| JP | 2008-523254 A | | 7/2008 | |
| JP | 2011015818 A | * | 1/2011 | |
| JP | 2012-197521 A | | 10/2012 | |
| JP | 2016-092009 A | | 5/2016 | |
| JP | 2018-102964 A | | 7/2018 | |
| KR | 10-2013-0141283 A | | 12/2013 | |
| KR | 20130141283 A | * | 12/2013 | ............... A61B 5/11 |
| TW | I 285227 B | | 8/2007 | |
| WO | WO-0102052 A2 | * | 1/2001 | ........... A61N 1/0452 |
| WO | 2016/114339 A1 | | 7/2016 | |
| WO | WO-2017010236 A1 | * | 1/2017 | ............. A41D 31/00 |
| WO | 2017/104596 A1 | | 6/2017 | |
| WO | 2017/119489 A1 | | 7/2017 | |
| WO | 2018/037855 A1 | | 3/2018 | |

OTHER PUBLICATIONS

International Search Report issued in corresponding International Patent Application No. PCT/JP2019/041420, dated Jan. 28, 2020, with English translation.
Extended European Search Report issued in corresponding European Patent Application No. 19876609.9-1113, dated Jul. 7, 2022.
Japanese Office Action dated Nov. 7, 2023 in Japanese Patent Application No. 2020-553416, w/English MT.
Office Action received in corresponding Korean Patent Application No. 10-2021-7012519, dated May 29, 2024.

* cited by examiner

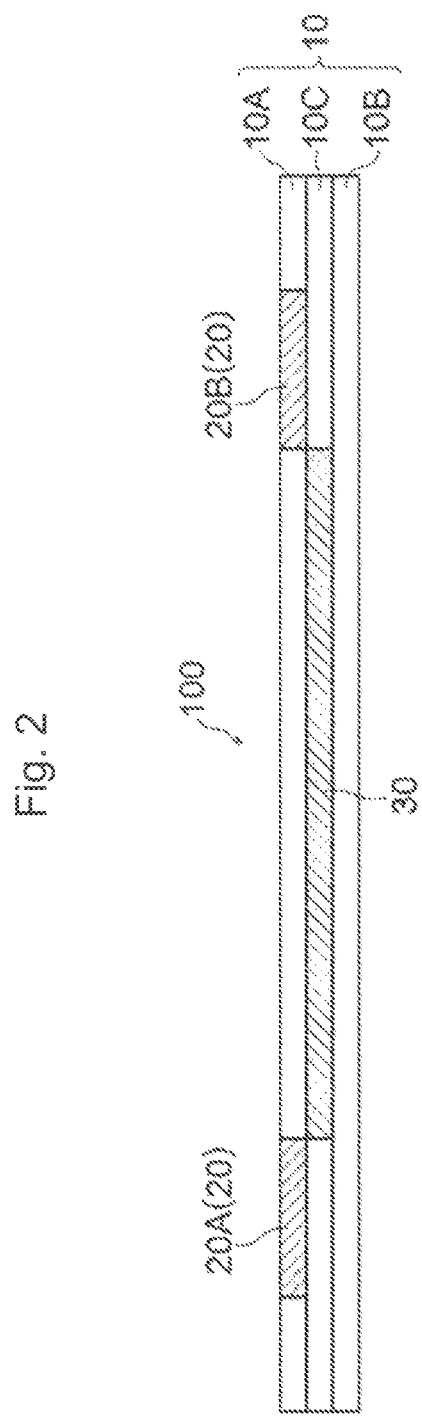

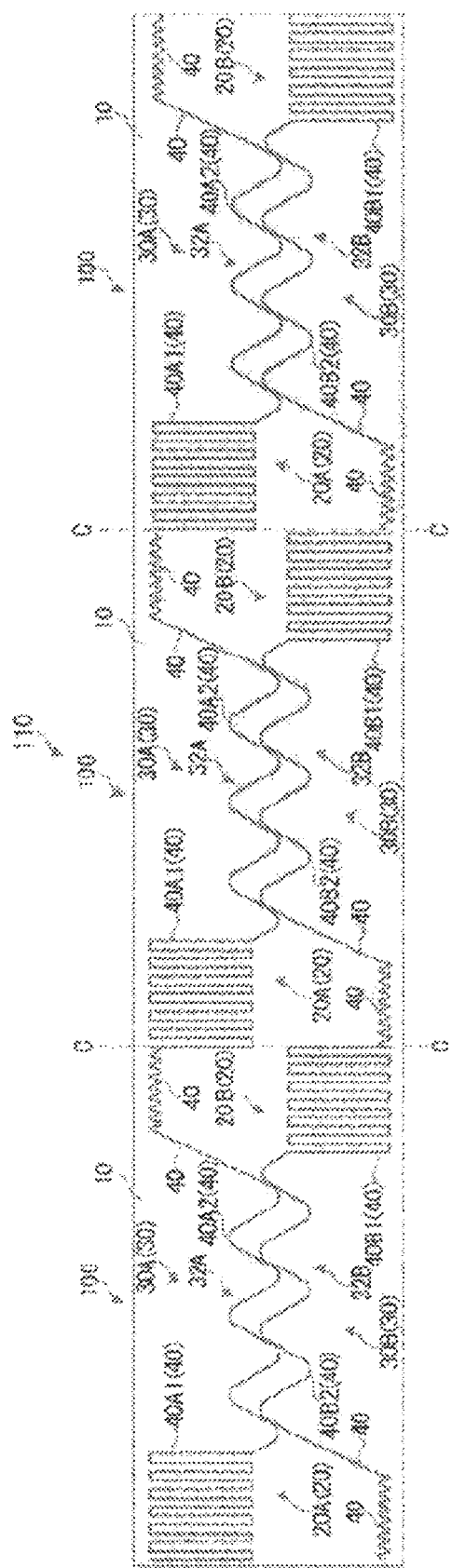

FABRIC MATERIAL WITH ELECTRODE WIRING

CROSS REFERENCE TO RELATED APPLICATIONS

This application is the U.S. National Phase under 35 U.S.C. § 371 of International Application No. PCT/JP2019/041420 filed on Oct. 22, 2019, which claims the benefit of Japanese Application No. 2018-199111, filed on Oct. 23, 2018, the entire contents of each are hereby incorporated by reference.

TECHNICAL FIELD

The present disclosure relates to a fabric material with an electrode wiring.

BACKGROUND ART

Fabric materials, utilized in wearable devices such as biomedical signal measurement instruments, have been conventionally known. For example, Patent Document 1 discloses a conductive fabric material in which a wiring including a first insulation layer, a conductive layer, and a second insulation layer is disposed on a fabric material. Patent Document 1 describes that the conductive fabric material of Patent Document 1 is useful in a wearable device capable of measuring biological information such as an electrocardiogram, a respiratory rate, a sweat rate, a body temperature, or an elbow angle (exercise quantity) by being worn as clothes.

Patent Document 1: WO 2016/114339

SUMMARY OF INVENTION

Technical Problem

Many sensors including resin films (films with resins such as silicon rubber and urethane) as base materials have been developed as sensors having switching functions, such as stretchable sensors.

However, affixation of a sensor to clothes or the like with an adhesive, a thermal melting resin, or the like is required for using a sensor, including a resin film as a base material, as a wearable device. A portion affixed with the sensor loses breathability, and may cause the clothes to uncomfortable to wear.

Therefore, a fabric material having a switching function is demanded under present circumstances. Such a fabric material having a switching function can also be utilized as a switching element such as a load sensor, for an application other than wearable devices, and has a high utility value.

Thus, an object of the disclosure is to provide a fabric material with an electrode wiring, having a switching function.

Solution to Problem

The problem described above is solved by the following means.

<1>
A fabric material with an electrode wiring, including:
a fabric material body with stretchability;
a first electrode portion that is disposed on a surface or in an interior of the fabric material body, and that includes a conductive linear body;
a first wiring portion that is disposed on the surface or in the interior of the fabric material body so as to be electrically connected to the first electrode portion, and that includes a conductive linear body;
a second electrode portion that is disposed on the surface or in the interior of the fabric material body, and that includes a conductive linear body; and
a second wiring portion that is disposed on the surface or in the interior of the fabric material body so as to be electrically connected to the second electrode portion, and that includes a conductive linear body,
wherein a resistance value between the first electrode portion and the second electrode portion is varied by stretching the fabric material with an electrode wiring.

<2>
The fabric material with an electrode wiring according to <1>, wherein
the first wiring portion and the second wiring portion are separately disposed,
the first wiring portion and the second wiring portion are spaced from each other by stretching the fabric material with an electrode wiring in a case in which the first wiring portion and the second wiring portion are disposed so that at least a part of the first wiring portion and the second wiring portion come into contact with each other before the fabric material with an electrode wiring is stretched, and
at least a part of the first wiring portion and the second wiring portion are brought into contact with each other by stretching the fabric material with an electrode wiring in a case in which the first wiring portion and the second wiring portion are disposed to be spaced from each other before the fabric material with an electrode wiring is stretched.

<3>
The fabric material with an electrode wiring according to <1> or <2>, wherein
the first wiring portion and the second wiring portion are separately disposed,
a contact region between the first wiring portion and the second wiring portion is decreased in a stepwise manner by stretching the fabric material with an electrode wiring in a case in which the first wiring portion and the second wiring portion are disposed so that at least a part of the first wiring portion and the second wiring portion come into contact with each other before the fabric material with an electrode wiring is stretched, and
the contact region between the first wiring portion and the second wiring portion is increased in a stepwise manner by stretching the fabric material with an electrode wiring in a case in which the first wiring portion and the second wiring portion are disposed to be spaced from each other before the fabric material with an electrode wiring is stretched.

<4>
The fabric material with an electrode wiring according to <1>, wherein
the first wiring portion and the second wiring portion are integrally disposed, and
a conduction path between the first wiring portion and the second wiring portion is prolonged by stretching the fabric material with an electrode wiring.

<5>
The fabric material with an electrode wiring according to any one of <1> to <4>, wherein the fabric material with an electrode wiring has a range of a stretching rate that the resistance value between the first electrode portion and the second electrode portion is varied by two times or more, or by ½ or less, in a range of ±5% in which the stretching rate varies, by stretching the fabric material with an electrode wiring to a maximum stretching rate.

<6>

The fabric material with an electrode wiring according to any one of <1> to <5>, wherein the resistance value between the first electrode portion and the second electrode portion varies in a stepwise manner according to the stretching rate of the fabric material with an electrode wiring.

<7>

The fabric material with an electrode wiring according to any one of <1> to <6>, wherein electrical connection between the first electrode portion and the second electrode portion is changed to electrical disconnection between the first electrode portion and the second electrode portion, or electrical disconnection between the first electrode portion and the second electrode portion is changed to electrical connection between the first electrode portion and the second electrode portion, by stretching the fabric material with an electrode wiring.

<8>

The fabric material with an electrode wiring according to any one of <1> to <7>, wherein a part of the conductive linear body in at least one of the first electrode portion or the second electrode portion is bound by a yarn of the fabric material body.

<9>

The fabric material with an electrode wiring according to <8>, wherein the fabric material body is interwoven, woven, or embroidered with the conductive linear body in at least one of the first electrode portion or the second electrode portion.

<10>

The fabric material with an electrode wiring according to any one of <1> to <9>, wherein a part of the conductive linear body is bound by a yarn of the fabric material body in at least one of the first wiring portion or the second wiring portion.

<11>

The fabric material with an electrode wiring according to <10>, wherein the fabric material body is interwoven, woven, or embroidered with the conductive linear body in at least one of the first wiring portion or the second wiring portion.

<12>

The fabric material with an electrode wiring according to any one of <1> to <11>, wherein at least one of the first wiring portion or the second wiring portion is disposed in the interior of the fabric material body.

<13>

The fabric material with an electrode wiring according to any one of <1> to <12>, wherein the conductive linear body contained in at least one of the first electrode portion, the second electrode portion, the first wiring portion, or the second wiring portion is a conductive linear body including a carbon nanotube yarn.

Advantageous Effects of Invention

In accordance with the disclosure, a fabric material with an electrode wiring, having a switching function, can be provided.

BRIEF DESCRIPTION OF DRAWINGS

FIG. 2 is a schematic cross-sectional view illustrating the fabric material with an electrode wiring according to the embodiment.

FIG. 14 is a schematic plan view for explaining an example of a method of producing the fabric material with an electrode wiring according to the embodiment.

DESCRIPTION OF EMBODIMENTS

Figure 1A:
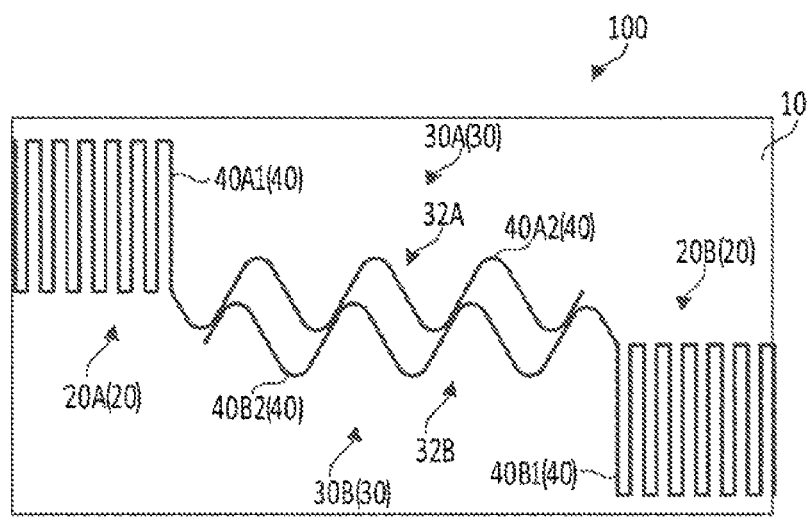
FIG. 1A is a schematic plan view illustrating a fabric material with an electrode wiring according to the present embodiment.

An embodiment which is an example of the disclosure will be described in detail below.

In the present specification, members having the substantially same function are denoted by the same reference character in all the drawings, and any description overlapped may be omitted.

A numerical range expressed by "x to y" means a numerical range including the values of x and y in the range as the minimum and maximum values, respectively.

A fabric material with an electrode wiring according to the present embodiment includes:
a fabric material body with stretchability;
a first electrode portion that is disposed on a surface or in the interior of the fabric material body, and that includes a conductive linear body;
a first wiring portion that is disposed on the surface or in the interior of the fabric material body so as to be electrically connected to the first electrode portion, and that includes a conductive linear body;
a second electrode portion that is disposed on the surface or in the interior of the fabric material body, and that includes a conductive linear body; and
a second wiring portion that is disposed on the surface or in the interior of the fabric material body so as to be electrically connected to the second electrode portion, and that includes a conductive linear body.

In the fabric material with an electrode wiring according to the embodiment, a resistance value between the first electrode portion and the second electrode portion is varied by stretching the fabric material with an electrode wiring.

The fabric material with an electrode wiring according to the embodiment can perform a switching function by detecting a variation in resistance value between the first electrode portion and the second electrode portion by stretching the fabric material with an electrode wiring.

In the present specification, the phrase "fabric material body" represents a fabric material, on which a conductive linear body is disposed.

The phrase "resistance value between first electrode portion and second electrode portion is varied" means that 1) a resistance value is increased or decreased in a state in which electrical connection between the first electrode portion and the second electrode portion is achieved, or 2) the state of electrical connection between the first electrode portion and the second electrode portion is changed to the state of electrical disconnection between the first electrode portion and the second electrode portion, or the state of electrical disconnection between the first electrode portion and the second electrode portion is changed to the state of electrical connection between the first electrode portion and the second electrode portion. The variation in resistance value excludes variations in resistance value, caused by damage to the electrode portions, the wiring portions, and the joint portions between the electrode portions and the wiring portions.

The phrase "at least a part of first wiring portion and second wiring portion come into contact with each other" also includes an aspect in which, in a case in which a wiring portion (for example, a third wiring portion) other than the first wiring portion and the second wiring portion is included, at least the part of the first wiring portion and the second wiring portion come into contact with each other via the other wiring portion.

The phrase "electrode portion or wiring portion is disposed on surface of fabric material body" represents that the electrode portion or the wiring portion (i.e., a conductive linear body) is disposed on a fabric material layer included in the front and back surfaces of the fabric material body (also including a fabric material layer partly included in the front and back surfaces). In other words, the phrase "electrode portion or wiring portion is disposed on surface of fabric material body" represents that the electrode portion or the wiring portion (i.e., a conductive linear body) is disposed in a state in which at least a part of the conductive linear body included in the electrode portion or the wiring portion is exposed from the fabric material body.

The phrase "electrode portion or wiring portion is disposed in interior of fabric material body" represents that the electrode portion or the wiring portion (i.e., a conductive linear body) is disposed in the inner layer of the fabric material body, for example, in a fabric material layer, which is the inner layer of the fabric material body, or between fabric material layers.

An example of the fabric material with an electrode wiring according to the embodiment will be described below with reference to the drawings.

A fabric material 100 with an electrode wiring according to the embodiment includes, for example, a fabric material body 10 with stretchability, electrode portions 20, and wiring portions 30, as illustrated in FIGS. 1A to 2.

Fabric Material Body

The fabric material body 10 includes, for example, fabric material layers, which are three-ply (three-layer), of a front surface fabric material layer 10A included in a front surface, a back surface fabric material layer 10B included in a back surface, and an intermediate fabric material layer 10C between the front surface fabric material layer 10A and the back surface fabric material layer 10B.

In addition to the fabric material layers which are three-ply, the fabric material body 10 may include, for example, fabric material layers which are one-ply (single-layer), two-ply (two-layer), or four- or multi-ply (four- or multi-layer).

The multi-ply fabric material body 10 including fabric materials layers which are two- or multi-layer may be produced by, for example, a technique in which each fabric material layer is produced and then stitched up. The multi-ply fabric material body 10 may be collectively produced by a weaving-knitting machine.

Typical examples of the fabric material body 10 include woven-knitted articles. The fabric material body 10 may be a non-woven fabric.

Examples of the woven-knitted articles include: woven articles made by plain weaving, diagonal weaving, satin weaving, well-known applied weaving, and the like; and knitted articles made by weft knitting, warp knitting, lace knitting, well-known applied knitting, and the like.

The yarn (linear body) included in the fabric material body 10 is an insulated yarn. The insulated yarn means a yarn having a line resistance of $1.0 \times 10^6$ $\Omega$/cm or more. The line resistance of the insulated yarn is a line resistance measured by the same method as a method by which the line resistance of a conductive linear body described below is measured.

The fabric material body 10 is a fabric material with stretchability. In other words, the fabric material 100 with an electrode wiring has stretchability.

The fabric material body 10 with stretchability can be realized by applying a woven-knitted article using an elastic yarn.

Examples of the elastic yarn include a covered yarn (single covered yarn or double covered yarn) formed by winding an inelastic yarn around the outer periphery of the elastic yarn in coil form, a core-spun yarn twisted by finely spinning an elastic yarn and an inelastic yarn, an air-interlaced covered yarn formed by winding an inelastic yarn around the outer periphery of an elastic yarn using a compressed-air nozzle, and a twisted yarn formed by twisting an elastic yarn and an inelastic yarn.

Examples of the elastic yarn include a yarn of a fiber exhibiting so-called rubber-like elasticity, such as a polyurethane elastic fiber, a polyester elastic fiber, or a polyamide elastic fiber.

Examples of the inelastic yarn include a yarn of a synthetic fiber (polyester fiber, polyamide fiber, acrylic fiber, polypropylene fiber, or rayon fiber), or a natural fiber (a fiber of cotton, silk, hemp, wool, or the like).

Electrode Portions and Wiring Portions

The electrode portions 20 include a first electrode portion 20A and a second electrode portion 20B.

The first electrode portion 20A and the second electrode portion 20B are disposed on one and the other of twin corners facing each other on a diagonal line of the fabric material body 10, for example, in planar view of the fabric material 100 with an electrode wiring, respectively. However, the arrangement positions of the first electrode portion 20A and the second electrode portion 20B are not the particularly limited, but are preferably arrangement positions at which a resistance value between the first electrode portion 20A and the second electrode portion 20B varies in the case of stretching the fabric material 100 with an electrode wiring.

Three or more electrode portions 20 may be disposed depending on a purpose.

The electrode portions 20 are disposed on the front surface fabric material layer 10A of the fabric material body 10. In other words, the electrode portions 20 are disposed on the surface of the fabric material body 10.

The electrode portions 20 may be disposed on the intermediate fabric material layer 10C of the fabric material body 10. In other words, the electrode portions 20 may be disposed in the interior of the fabric material body 10. This is because a pin-shaped electrode or the like enables connection even in a case in which the electrode portions 20 are disposed in the interior of the fabric material body 10.

The wiring portions 30 include a first wiring portion 30A and a second wiring portion 30B.

The first wiring portion 30A is electrically connected to the first electrode portion 20A.

The second wiring portion 30B is electrically connected to the second electrode portion 20B.

The first wiring portion 30A and the second wiring portion 30B are separately disposed so that at least a part of the first wiring portion 30A and the second wiring portion 30B come into contact with each other before the fabric material 100 with an electrode wiring is stretched.

The first wiring portion 30A extends, for example, from the first electrode portion 20A toward one side of the fabric material body 10, on which the second electrode portion 20B exists. The first wiring portion 30A includes at least a wavy portion 32A in which a conductive linear body 40A2 is disposed in wavy form, on the central portion of the fabric material body 10.

The second wiring portion 30B extends, for example, from the second electrode portion 20B toward one side of the fabric material body 10, on which the first electrode portion 20A exists. The second wiring portion 30B also includes at least a wavy portion 32B in which a conductive linear body 40B2 is disposed in wavy form, on the central portion of the fabric material body 10.

The wavy portion 32A of the first wiring portion 30A and the wavy portion 32B of the second wiring portion 30B are brought into point contact or line contact with each other before the fabric material 100 with an electrode wiring is stretched.

A configuration in which neither the first wiring portion 30A nor the second wiring portion 30B includes a wavy portion in which the conductive linear body 40A2 or the conductive linear body 40B2 is disposed in wavy form, and each of the first wiring portion 30A and the second wiring portion 30B includes only a straight-line portion in which the conductive linear body 40A2 or the conductive linear body 40B2 is disposed in a straight line is also acceptable. Each of the first wiring portion 30A and the second wiring portion 30B includes a bent portion in which the conductive linear body 40A2 or the conductive linear body 40B2 is bent.

The wiring portions 30 are disposed in the interior of the fabric material body 10. Specifically, the wiring portions 30 can be disposed in the interior of the fabric material body 10 by disposing the wiring portions 30 on the intermediate fabric material layer 10C, which is the fabric material layer (including a fabric material layer which is partly an inner layer) of the inner layer of the fabric material body 10 including, for example, three fabric material layers. The wiring portions 30 may also be disposed between the fabric material layers of the fabric material body 10 including, for example, the two fabric material layers.

The wiring portions 30 may be disposed on a surface of the fabric material body 10. For example, the wiring portions 30 may be disposed on the front surface fabric material layer 10A or back surface fabric material layer 10B of the fabric material body 10 including three fabric material layers. However, it is preferable to dispose the wiring portions 30 in the interior of the fabric material body 10 from the viewpoint of attempting insulation from the outside by the fabric material body 10.

Each of the electrode portions 20 and the wiring portions 30 includes a conductive linear body 40. In other words, regions on which such conductive linear bodies 40 are placed are regarded as the electrode portions 20 and the wiring portions 30.

Specifically, for example, the first electrode portion 20A includes a conductive linear body 40A1. The first wiring portion 30A includes the conductive linear body 40A2 in which the conductive linear body 40A1 of the first electrode portion 20A extends. In other words, a set of the first electrode portion 20A and the first wiring portion 30A includes at least one identical conductive linear body 40.

For example, the second electrode portion 20B includes a conductive linear body 40B1. The second wiring portion 30B includes the conductive linear body 40B2 in which the conductive linear body 40B1 of the second electrode portion 20B extends. In other words, a set of the second electrode portion 20B and the second wiring portion 30B includes at least one identical conductive linear body 40.

Each of the set of the first electrode portion 20A and the first wiring portion 30A, and the set of the second electrode portion 20B and the second wiring portion 30B includes the one identical conductive linear body 40, whereby poor connection between the electrode portions 20 and the wiring portions 30 is suppressed.

The one identical conductive linear body 40 also includes a linear body formed by bonding ends of conductive linear bodies 40 by knotting, splicing, or the like with using neither a connection material (solder, conductive paste, or the like) nor a connection member (caulking, a connector, or the like) other than a linear body.

However, each of the electrode portions 20 and the wiring portions 30 may include a plurality of conductive linear bodies 40. Each of the set of the first electrode portion 20A and the first wiring portion 30A, and the set of the second electrode portion 20B and the second wiring portion 30B need not include one identical conductive linear body 40. For example, in each of the set of the first electrode portion 20A and the first wiring portion 30A, and the set of the second electrode portion 20B and the second wiring portion 30B, ends of conductive linear bodies 40 may be linked to each other by a connection material (solder, conductive paste, or the like) or a connection member (caulking, a connector, or the like) other than a linear body.

In at least one of such an electrode portion 20 or such a wiring portion 30, for example, at least a part of the conductive linear body 40 is bound by a yarn of the fabric material body 10. Such a form is preferred from the viewpoint of enabling the conductive linear bodies 40 functioning as conductive materials to be also used as means of fixing the electrode portions 20 and/or the wiring portions 30 to the fabric material body 10. The conductive linear bodies 40 bound to the fabric material body 10 may be one identical conductive linear body 40 included in both such an electrode portion 20 and such a wiring portion 30, or may be separate conductive linear bodies 40 of which each is included only in either such an electrode portion 20 or such a wiring portion 30.

In at least one of such an electrode portion 20 or such a wiring portion 30, the conductive linear body 40 need not be bound by a yarn of the fabric material body 10. For example, in a case in which the electrode portions 20 and/or the wiring portions 30 are fixed to the fabric material body 10 with an adhesive, or in a case in which the electrode portions 20 or the wiring portions 30 is sewn on the fabric material body 10 by an insulated yarn, the electrode portions 20 and/or the wiring portions 30 can be fixed to the fabric material body 10 even in a case in which the conductive linear bodies 40 are not bound by a yarn of the fabric material body 10.

For example, a rectangular region is formed by arranging the conductive linear bodies 40 that are repeatedly bent or curved at 180°. The rectangular region is formed by binding a part of such a conductive linear body 40 to a yarn of the front surface fabric material layer 10A of the fabric material body 10. The rectangular region is regarded as a surface-shaped electrode portion 20.

A region formed by spirality arranging the conductive linear bodies 40 may be regarded as such an electrode portion 20. An optional plane shape (a polygonal shape, a circular shape, or the like) formed by arranging the conductive linear bodies 40 that are bent or curved may be regarded as such an electrode portion 20.

A region in which the conductive linear body 40 extends from the electrode portion 20 in a linear, wavy, or bent shape, or a combination thereof is formed. The region is formed by binding a part of the conductive linear body 40 to a yarn of the intermediate fabric material layer 10C of the fabric material body 10. The region is regarded as such a wiring portion 30.

Figure 3:
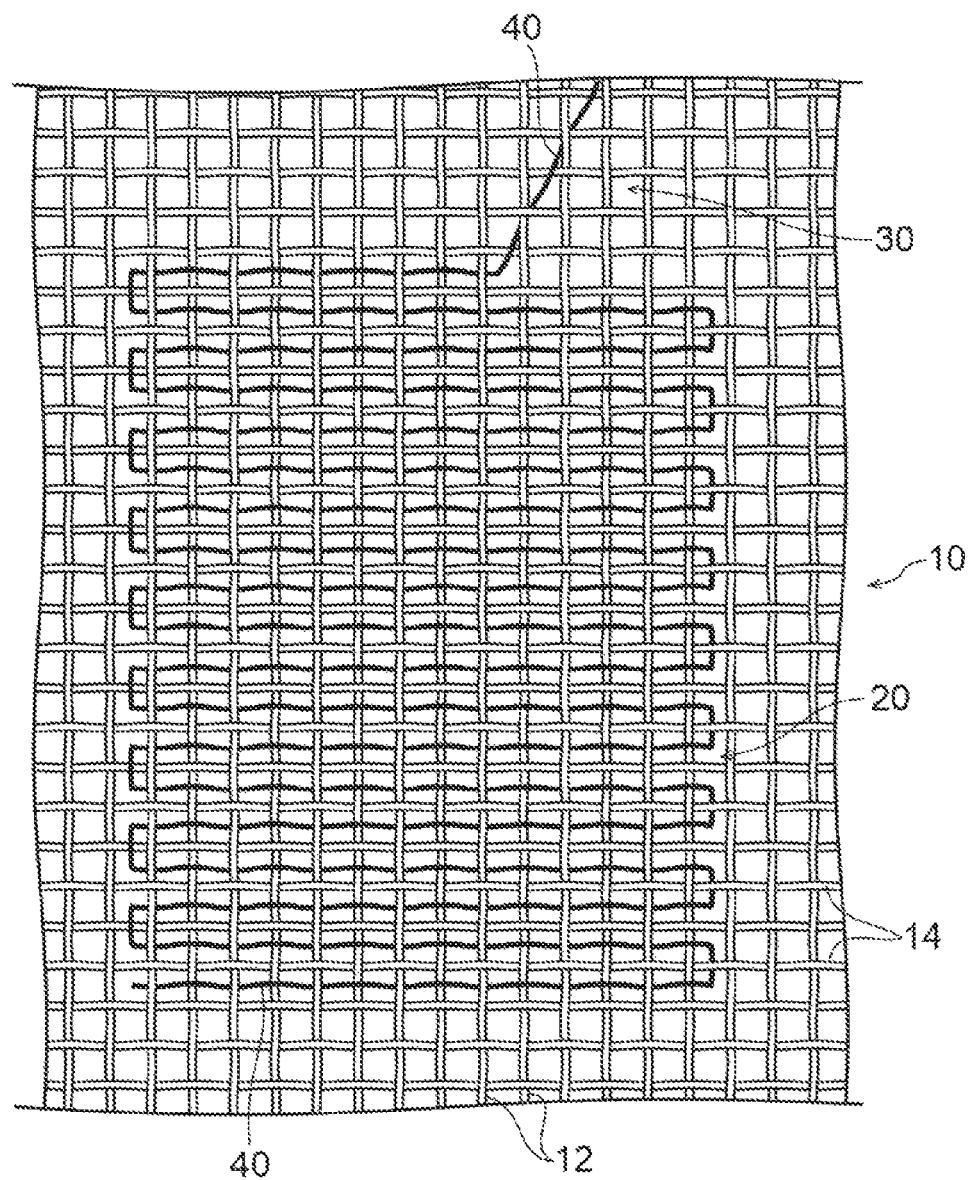
FIG. 3 is a schematic plan view illustrating an example in which the fabric material with an electrode wiring according to the embodiment is interwoven with a conductive linear body.

Specifically, it is preferable to form an electrode portion 20 and/or a wiring portion 30 by interweaving the woven texture of a woven article, woven with the warp and the weft, with a conductive linear body 40 as illustrated in FIG. 3, in a case in which the fabric material body 10 is a woven article, from the view point of enabling the electrode portion 20 and/or the wiring portion 30 to be simultaneously formed in the case of forming the fabric material body 10 with a woven fabric, and from the viewpoint of improving the integration of the fabric material body 10, the electrode portions 20, and/or the wiring portion 30.

Figure 4:
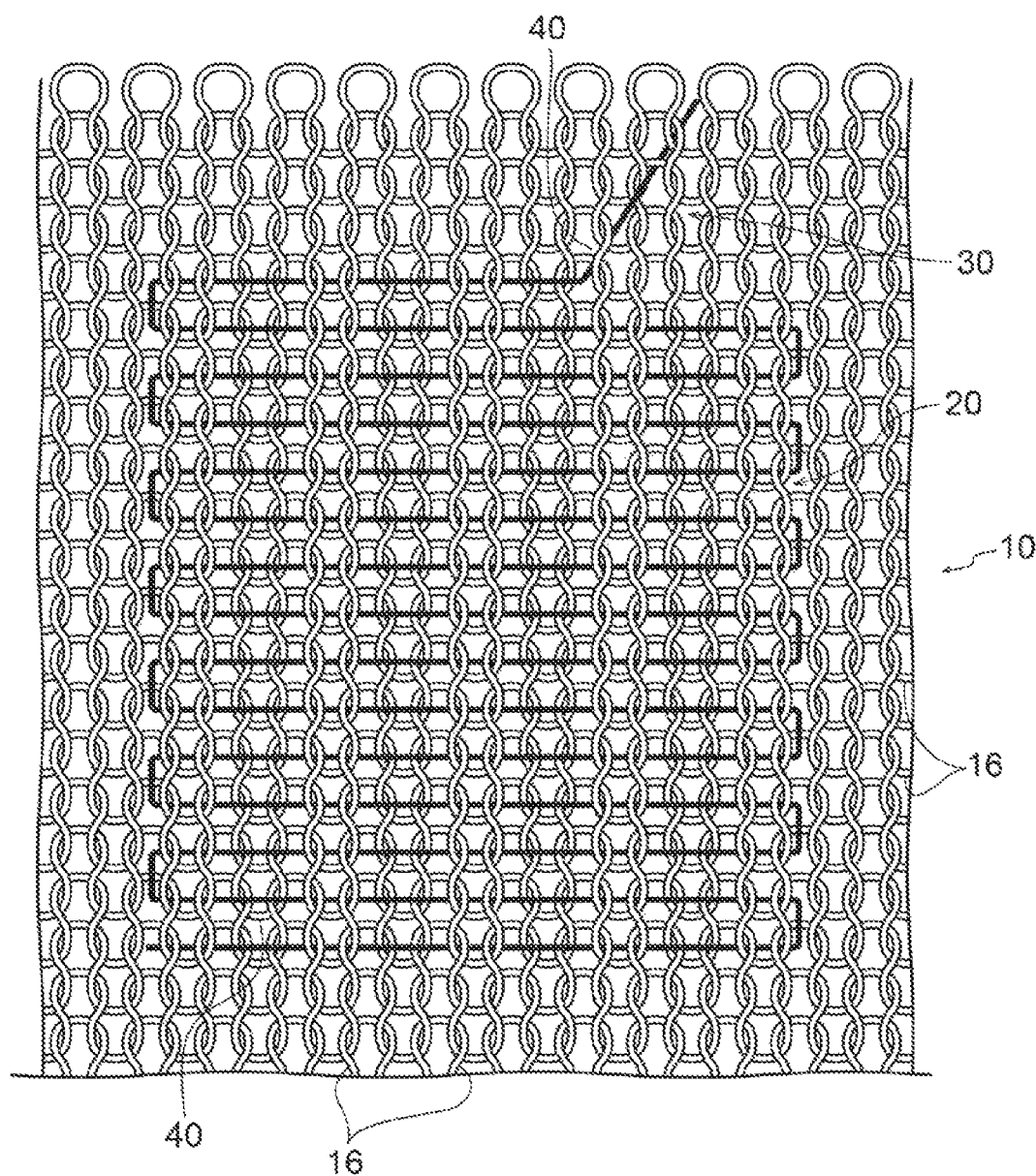
FIG. 4 is a schematic plan view illustrating an example in which the fabric material with an electrode wiring according to the embodiment is woven with a conductive linear body.

It is preferable to form an electrode portion 20 and/or a wiring portion 30 by weaving the braided texture of a knitted article, woven with loop-shaped yarns, with a conductive linear body 40 to have the shape described above, as illustrated in FIG. 4, in a case in which the fabric material body 10 is a knitted article, from the viewpoint of enabling the electrode portion 20 and/or the wiring portion 30 to be simultaneously formed in the case of forming the fabric material body 10 by weaving, and from the viewpoint of improving the integration of the fabric material body 10, the electrode portion 20, and/or wiring portion 30. For example, knitting with some yarns together, plating knitting, inlay knitting, or the like can be adopted in the case of weaving the network texture of a knitted article with the conductive linear body 40. FIG. 4 illustrates an example in which the inlay knitting is adopted to weave the conductive linear body 40.

Figure 5:
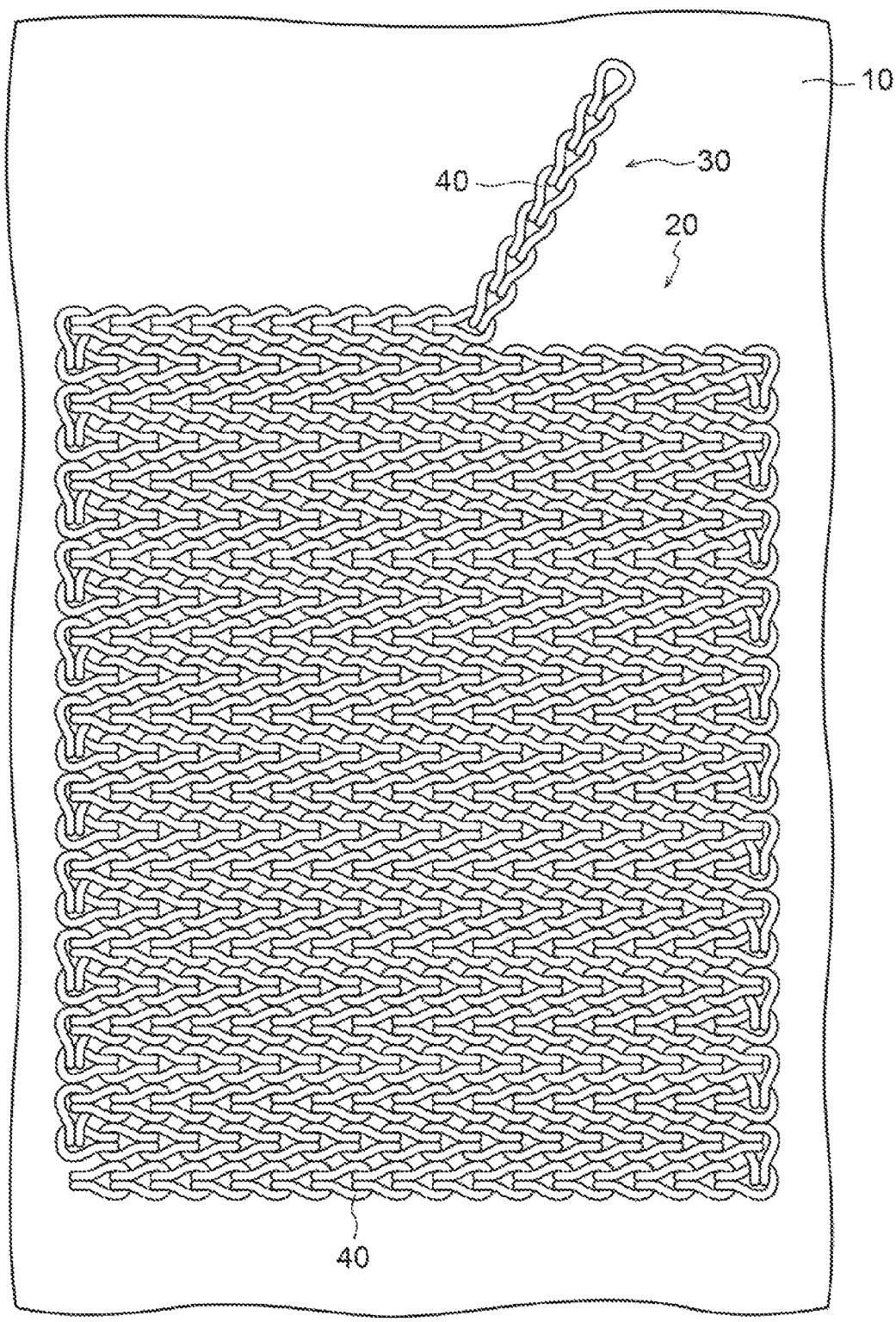
FIG. 5 is a schematic plan view illustrating an example in which the fabric material with an electrode wiring according to the embodiment is embroidered with a conductive linear body.

It is preferable to embroider the fabric material body 10 with a conductive linear body 40 in the shape described above to form an electrode portion 20 and/or a wiring portion 30, as illustrated in FIG. 5, from the viewpoint of enabling the electrode portion 20 and/or the wiring portion 30 to be simultaneously fixed to the fabric material body 10 in the case of forming the electrode portion 20 and/or the wiring portion 30. Examples of embroidery techniques that can be adopted include well-known stitches such as running stitch, coating stitch, backstitch, chain stitch, and outlinestitch. FIG. 5 illustrates an example in which the chain stitch is adopted to embroider the conductive linear body 40.

It is preferable to sew and fix an electrode portion 20 and/or a wiring portion 30 on the fabric material body 10 by a conductive linear body 40 from the viewpoint of enabling a conductive linear body 40 included in the electrode portion 20 and/or the wiring portion 30, and the conductive linear body 40, by which the electrode portion 20 and/or the wiring portion 30 are fixed, to be common to each other.

Examples of the aspect in which the electrode portion 20 and/or the wiring portion 30 are sewn and fixed by the conductive linear body 40 include an aspect in which an electrode portion 20 and a wiring portion 30 are continuously formed a woven article interwoven with a conductive linear body 40 or a knitted article woven with the conductive linear body 40, and the electrode portion 20 and the wiring portion 30 are sewn on the fabric material body 10 by the conductive linear body 40.

In FIG. 3, reference numeral 12 denotes the warps included in the fabric material body 10 (woven article), and reference numeral 14 denotes the wefts included in the fabric material body 10 (woven article). In FIG. 4, reference numeral 16 denotes yarns included in the fabric material body 10 (woven article).

In a case in which an elastic yarn is adopted as a yarn included in the fabric material body 10, it is preferable to interwoven or weave the fabric material body 10 with the conductive linear body while forming a woven-knitted article in a state in which the elastic yarn is stretched.

Conductive Linear Body

The conductive linear bodies included in the electrode portions 20 and the wiring portions 30 are not particularly limited as long as having conductivity. Examples of the conductive linear bodies include a linear body including a metal wire and a linear body including a conductive yarn. The conductive linear bodies 40 may be linear bodies including a metal wire and a conductive yarn (such as linear bodies formed by twisting a metal wire and a conductive yarn).

Since both the linear body including a metal wire and the linear body including a conductive yarn have high electrical conductivity, application of the linear bodies as the conductive linear bodies 40 facilitates a reduction in the resistances of the electrode portions 20 and the wiring portions 30.

Examples of the metal wire include a wire including a metal such as copper, aluminum, tungsten, iron, molybdenum, nickel, titanium, silver, or gold, or an alloy including two or more metals (for example, a steel such as stainless steel or carbon steel, brass, phosphor bronze, zirconium-copper alloy, beryllium-copper, iron-nickel, nichrome, nickel-titanium, kanthal, hastelloy, rhenium-tungsten, or the like). The metal wire may be plated with tin, zinc, silver, nickel, chromium, nickel-chrome alloy, solder, or the like, or may include a surface coated with a carbon material or polymer described below.

Examples of the metal wire include a metal wire coated with a carbon material. Metallic corrosion is suppressed in a case in which the metal wire is coated with such a carbon material.

Examples of the carbon material with which the metal wire is coated include: amorphous carbons such as carbon black, activated carbon, hard carbon, soft carbon, mesoporous carbon, and carbon fiber; graphite; fullerene; graphene; and carbon nanotubes.

The linear body including a conductive yarn may be a linear body including one conductive yarn, or may be a linear body formed by twisting a plurality of conductive yarns. The linear body may be formed by twisting a conductive yarn and an insulated yarn. The linear body including a conductive yarn has an advantage in that the linear body has higher flexibility than the linear body including a metal wire, and precludes disconnection caused by interweaving, weaving, embroidering, or sewing the linear body on the fabric material body 10.

Examples of such conductive yarns include yarns including conductive fibers (metal fibers, carbon fibers, fibers of ionic conductive polymers, and the like), yarns including conductive fine particles (carbon nanoparticles, and the like), yarns including surfaces plated or vapor-deposited with metals (copper, silver, nickel, and the like), and yarns impregnated with metal oxides.

Particularly preferred examples of the linear body including a conductive yarn include a linear body including a yarn including carbon nanotubes as carbon nanoparticles (carbon nanotube yarn) (hereinafter also referred to as "carbon nanotube linear body").

The carbon nanotube linear body is obtained by drawing carbon nanotubes in sheet form from an end of a carbon nanotube forest (which is a grown body formed by growing a plurality of carbon nanotubes on a substrate to be oriented in a vertical direction with respect to the substrate, and may also be referred to as "array"), bundling up the drawn carbon nanotube sheet, and then twisting the bundle of the carbon nanotubes. In such production method, a ribbon-shaped carbon nanotube linear body is obtained in the case of applying no torsion in the twisting, whereas a yarn-shaped linear body is obtained in the case of applying torsion. The ribbon-shaped carbon nanotube linear body is a linear body that does not have a structure in which torsion is applied to an aggregate of a plurality of carbon nanotubes. In addition, such a carbon nanotube linear body can also be obtained by, for example, spinning from a dispersion liquid of carbon nanotubes. The production of the carbon nanotube linear body by the spinning can be performed by, for example, a method disclosed in U.S. Patent Publication No. US 2013/0251619 (Japanese Patent Application Laid-Open (JP-A) No. 2011-253140). It is desirable to use a yarn-shaped carbon nanotube linear body from the viewpoint of obtaining the uniformity of the diameter of the carbon nanotube linear body, while it is preferable to obtain a yarn-shaped carbon nanotube linear body by twisting a carbon nanotube sheet from the viewpoint of obtaining the carbon nanotube linear body having high fineness. The carbon nanotube linear body may be a linear body formed by twisting two or more carbon nanotube linear bodies together.

The carbon nanotube linear body may be a linear body including carbon nanotubes and a conductive material, other than carbon nanotubes, such as a metal, a conductive polymer, or graphene (hereinafter also referred to as "composite linear body"). In the composite linear body, the conductivity of the linear body is easily improved while maintaining the above-described features of a carbon nanotube linear body.

Examples of the composite linear body include (1) a composite linear body formed by carrying a single metal or a metal alloy on a surface of the forest, sheet, or bundle of the carbon nanotubes, or a twisted linear body by vapor deposition, ion plating, sputtering, wet plating, or the like in a process of obtaining a carbon nanotube linear body, in which carbon nanotubes are drawn in sheet form from an end of a carbon nanotube forest, and the drawn carbon nanotube sheet is bundled up, and the bundle of the carbon nanotubes is then twisted, (2) a composite linear body formed by twisting the bundle of carbon nanotubes with the linear body of a single metal, the linear body of a metal alloy, or a composite linear body, and (3) a composite linear body formed by twisting the linear body of a single metal, the linear body of a metal alloy, or a composite linear body, and a carbon nanotube linear body or composite linear body, in a case in which a linear body including a carbon nanotube and a metal is taken as an example. Like the composite linear body (1), a metal may be carried on the carbon nanotubes in the case of twisting the bundle of the carbon nanotubes in the composite linear body (2). The composite linear body (3) is a composite linear body in which two linear bodies are woven. However, the composite linear body (3) may be formed by weaving three or more of a carbon nanotube linear body, the linear body of a single metal, the linear body of a metal alloy, or a composite linear body as long as including at least one linear body of a single metal, at least one linear body of a metal alloy, or at least one composite linear body.

Examples of the metal of the composite linear body include a single metal such as gold, silver, copper, iron, aluminum, nickel, chromium, tin, or zinc, or an alloy including at least one of these single metals (copper-nickel-phosphorus alloy, copper-iron-phosphorus-zinc alloy, or the like).

Among these conductive linear bodies 40, conductive linear bodies including carbon nanotube yarns (in particular, a conductive linear body including only a carbon nanotube yarn, and a conductive linear body including a carbon nanotube yarn and a non-metal conductive material) are preferred.

For example, in the case of repeatedly stretching and shrinking a yarn of which the surface is plated or vapor-deposited with a metal (copper, silver, nickel, or the like), and a yarn impregnated with a metal oxide, the metal or the metal oxide is prone to be cracked. Thus, the yarns have low durability. In this regard, the carbon nanotube linear body has high resistance to bending, and a variation in the resistance value of a wiring portion is inhibited even in a case in which the fabric material 100 with an electrode wiring is repeatedly stretched and shrunk. The carbon nanotube linear body also has an advantage in that the carbon nanotube linear body also has high corrosion resistance.

The line resistance of such a conductive linear body 40 is preferably from $5.0 \times 10^{-3}$ Ω/cm to $1.0 \times 10^{3}$ Ω/cm, and more preferably from $1.0 \times 10^{-2}$ Ω/cm to $5.0 \times 10^{2}$ Ω/cm.

The line resistance of the conductive linear body 40 is measured as described below. First, silver pastes are applied to both ends of the conductive linear body 40, and the resistance of a portion between the silver pastes is measured to determine the resistance value (unit: Ω) of the conductive linear body 40. The line resistance of the conductive linear body 40 is calculated by dividing the obtained resistance value by a distance (cm) between the silver pastes.

Action of Fabric Material with Electrode Wiring

In the fabric material 100 with an electrode wiring according to the embodiment, at least a part (the wavy portions 32A and 32B in the embodiment) of the first wiring portion 30A and the second wiring portion 30B come into contact with each other before the fabric material 100 with an electrode wiring is stretched (see FIG. 1A). Specifically, at least a part of the conductive linear body 40A2 included in the first wiring portion 30A and the conductive linear body 40B2 included in the second wiring portion 30B come into contact with each other.

Figure 1B:
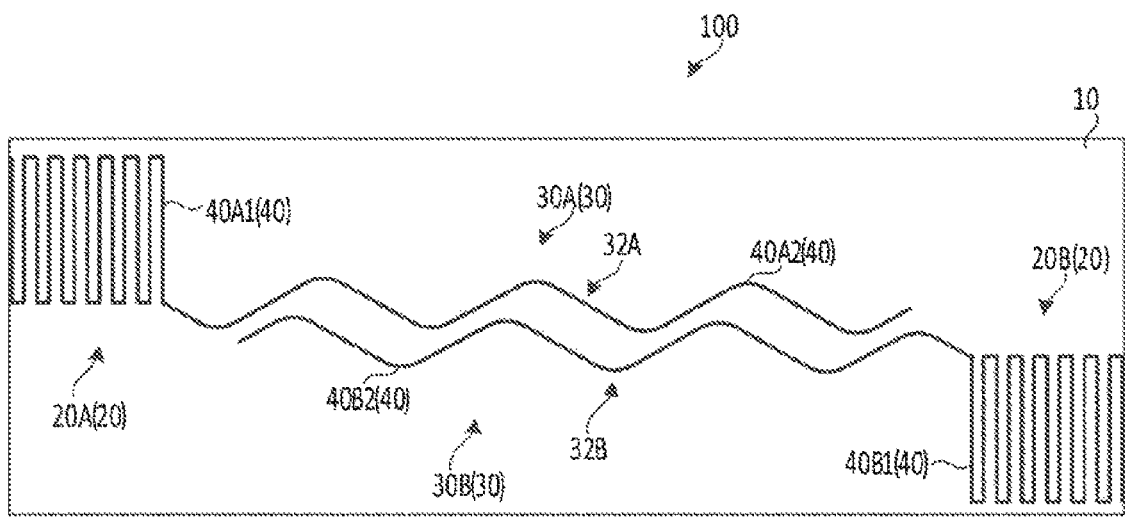
FIG. 1B is a schematic plan view illustrating the stretched state of the fabric material with an electrode wiring according to the embodiment.

In a case in which the fabric material 100 with an electrode wiring is stretched along the longitudinal direction of the fabric material, the first wiring portion 30A and the second wiring portion 30B, which come into contact with each other, are spaced from each other when a certain stretching rate is reached (see FIG. 1B). Specifically, the conductive linear body 40A2 included in the first wiring portion 30A and the conductive linear body 40B2 included in the second wiring portion 30B are spaced from each other.

More specifically, a period between the wavy portion 32A of the first wiring portion 30A and the wavy portion 32B of the second wiring portion 30B is prolonged, and an amplitude between the wavy portion 32A and the wavy portion 32B is decreased, in a case in which the fabric material 100 with an electrode wiring is stretched along the longitudinal direction of the fabric material. Thus, the first wiring portion 30A and the second wiring portion 30B are spaced from each other.

The stretching direction of the fabric material 100 with an electrode wiring is not limited to the longitudinal direction of the fabric material, but is preferably a direction at which a variation in resistance value caused by the stretching is intended to be detected. For example, the stretching direction may be a direction intersecting the longitudinal direction of the fabric material.

This operation allows a resistance value between the first electrode portion 20A and the second electrode portion 20B to be varied in a case in which the fabric material 100 with an electrode wiring is stretched. In other words, the resistance value is increased. Specifically, electrical connection between the first electrode portion 20A and the second electrode portion 20B is changed to electrical disconnection between the first electrode portion 20A and the second electrode portion 20B.

The fabric material 100 with an electrode wiring performs a switching function by detecting a variation in resistance value between the first electrode portion 20A and the second electrode portion 20B, caused by the stretching.

In a case in which the stretching of the fabric material 100 with an electrode wiring is canceled (i.e., the fabric material 100 with an electrode wiring is shrunk), at least a part of the first wiring portion 30A and the second wiring portion 30B, spaced from each other, come into contact with each other when a certain stretching rate is reached (see FIG. 1A). In other words, the resistance value is decreased. Specifically, electrical disconnection between the first electrode portion 20A and the second electrode portion 20B is changed to electrical connection between the first electrode portion 20A and the second electrode portion 20B.

The fabric material 100 with an electrode wiring performs a switching function by detecting a variation in resistance value between the first electrode portion 20A and the second electrode portion 20B, caused by the shrinking, as described above.

Figure 6:
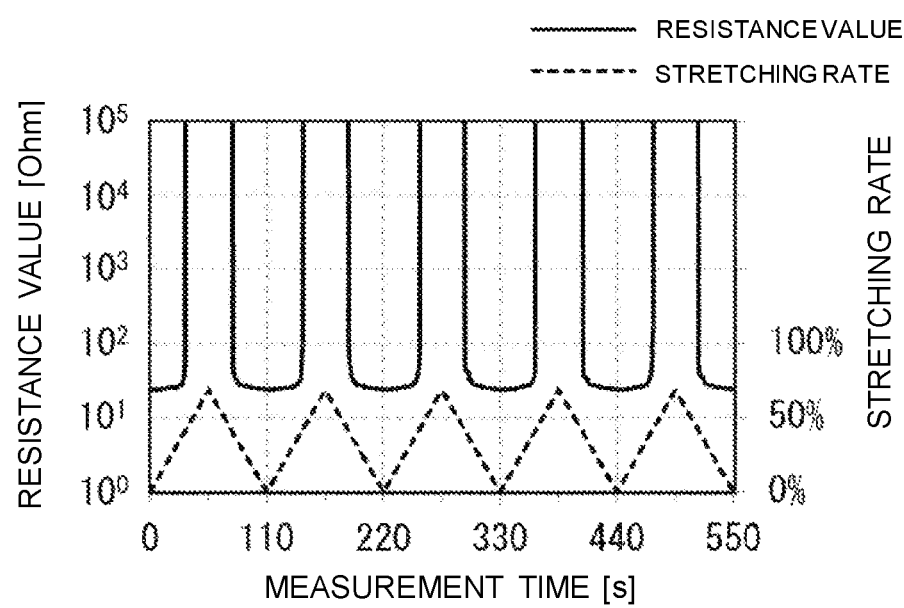
FIG. 6 is a view illustrating an example of "relationship between resistance value between first electrode portion and second electrode portion, and measurement time, and relationship between stretching rate and measurement time" in a case in which the stretching of a fabric material with an electrode wiring to a maximum stretching rate, and the shrinking of the fabric material are repeated five times.
Figure 7:
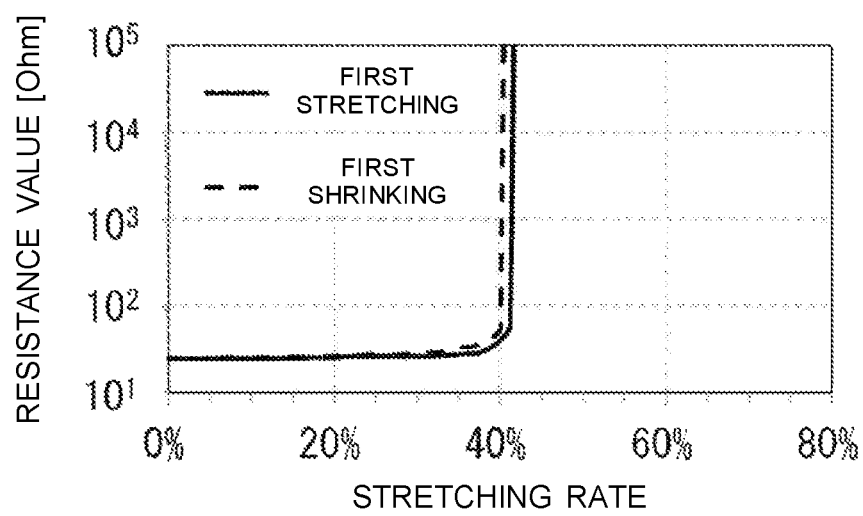
FIG. 7 is a view illustrating an example of "relationship between resistance value between first electrode portion and second electrode portion, and stretching rate" in the first stretching and shrinking, based on the results of FIG. 6.

FIG. 6 illustrates an example of "relationship between resistance value between first electrode portion 20A and second electrode portion 20B, and measurement time, and relationship between stretching rate and measurement time" in a case in which operation of stretching the fabric material 100 with an electrode wiring having a maximum stretching rate (=about 80%) to a stretching rate of 70% and then shrinking the fabric material 100 with an electrode wiring is repeated five times at a stretching velocity of 1 mm/s. FIG. 7 illustrates an example of "relationship between resistance value between first electrode portion 20A and second electrode portion 20B, and stretching rate" in the first stretching and shrinking, based on the results of FIG. 6.

As illustrated in FIGS. 6 to 7, the resistance value between the first electrode portion 20A and the second electrode portion 20B is varied after a certain stretching rate in a case in which the fabric material 100 with an electrode wiring is stretched and shrunk. Specifically, electrical connection between the first electrode portion 20A and the second electrode portion 20B is changed to electrical disconnection between the first electrode portion 20A and the second electrode portion 20B, and electrical disconnection between the first electrode portion 20A and the second electrode portion 20B is changed to electrical connection between the first electrode portion 20A and the second electrode portion 20B.

The fabric material 100 with an electrode wiring performs a switching function by detecting a variation in resistance value between the first electrode portion 20A and the second electrode portion 20B, caused by stretching and shrinking, as illustrated in FIGS. 6 to 7.

The measurement results of the variations in resistance value illustrated in FIGS. 6 to 7 reveal that the resistance value is increased in the stretching and decreased in the shrinking in a range of an average stretching rate of around 43.7%±5%.

Alternative Examples

The fabric material 100 with an electrode wiring according to the embodiment is not limited to the form described above, but may be modified or improved. Alternative examples of the fabric material 100 with an electrode wiring according to the embodiment will be described below. In the following description, the same members as those described in the form described above in the fabric material 100 with an electrode wiring according to the embodiment are denoted by the same reference characters in the figures, and the descriptions thereof are omitted or simplified.

First Alternative Example

Figure 8A:
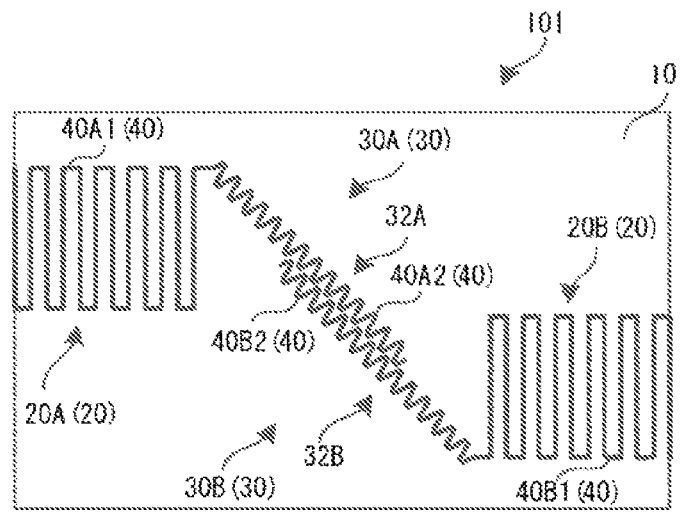
FIG. 8A is a schematic plan view illustrating a fabric material with an electrode wiring of a first alternative example.

The fabric material 100 with an electrode wiring according to the embodiment may be, for example, a fabric material 101 with an electrode wiring illustrated in FIG. 8A.

Specifically, the fabric material 101 with an electrode wiring includes a first wiring portion 30A and a second wiring portion 30B, disposed to be spaced from each other before the fabric material 101 with an electrode wiring is stretched, as illustrated in FIG. 8A. A wavy portion 32A of the first wiring portion 30A and a wavy portion 32B of the second wiring portion 30B face each other substantially in parallel, and are disposed to be spaced from each other.

Figure 8B:
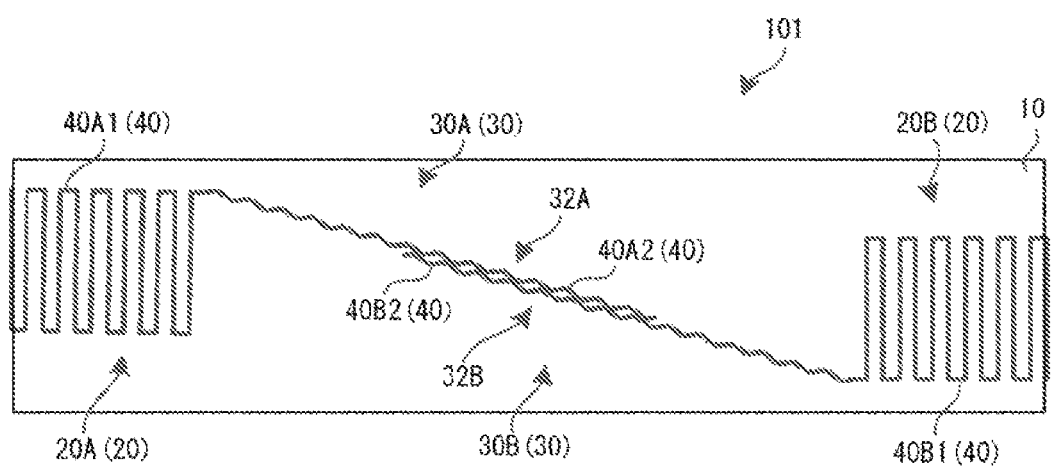
FIG. 8B is a schematic plan view illustrating the stretched state of the fabric material with an electrode wiring of the first alternative example.

In a case in which the fabric material 101 with an electrode wiring is stretched along the longitudinal direction of the fabric material, at least a part of the first wiring portion 30A and the second wiring portion 30B, spaced from each other, come into contact with each other when a certain stretching rate is reached (see FIG. 8B). Specifically, at least a part of a conductive linear body 40A2 included in the first wiring portion 30A and a conductive linear body 40B2 included in the second wiring portion 30B come into contact with each other.

More specifically, in a case in which the fabric material 101 with an electrode wiring is stretched along the longitudinal direction of the fabric material, the wavy portion 32A of the first wiring portion 30A and the wavy portion 32B of the second wiring portion 30B approach each other and come into contact with each other while prolonging the periods thereof and decreasing the amplitudes thereof.

This operation allows a resistance value between a first electrode portion 20A and a second electrode portion 20B to be varied in a case in which the fabric material 101 with an electrode wiring is stretched. In other words, the resistance value is decreased. Specifically, electrical disconnection between the first electrode portion 20A and the second electrode portion 20B is changed to electrical connection between the first electrode portion 20A and the second electrode portion 20B.

The fabric material 101 with an electrode wiring performs a switching function by detecting a variation in resistance value between the first electrode portion 20A and the second electrode portion 20B, caused by the stretching.

In a case in which the stretching of the fabric material 101 with an electrode wiring is canceled (i.e., the fabric material 101 with an electrode wiring is shrunk), the first wiring portion 30A and the second wiring portion 30B, coming into contact with each other, are spaced from each other when a certain stretching rate is reached (see FIG. 8A). In other words, the resistance value is increased. Specifically, electrical connection between the first electrode portion 20A and the second electrode portion 20B is changed to electrical disconnection between the first electrode portion 20A and the second electrode portion 20B.

The fabric material 101 with an electrode wiring performs a switching function by detecting a variation in resistance value between the first electrode portion 20A and the second electrode portion 20B, caused by the shrinking, as described above.

Second Alternative Example

Figure 9A:
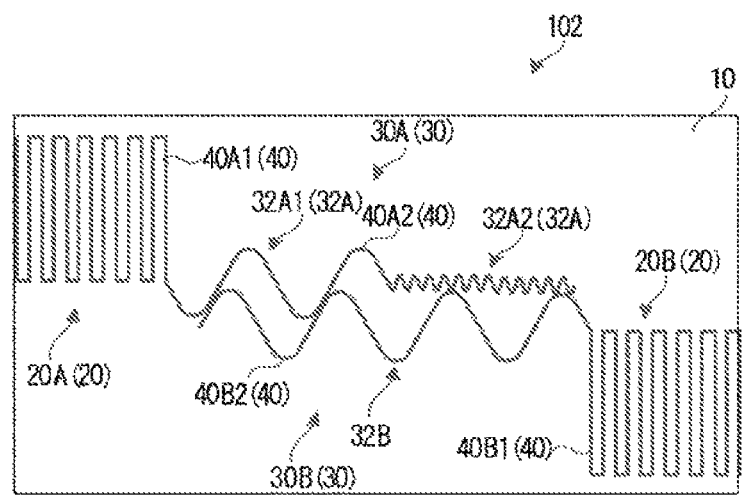
FIG. 9A is a schematic plan view illustrating a fabric material with an electrode wiring of a second alternative example.

The fabric material 100 with an electrode wiring according to the embodiment may be, for example, a fabric material 102 with an electrode wiring illustrated in FIG. 9A.

Specifically, the fabric material 102 with an electrode wiring includes a first wavy portion 32A1 and a second wavy portion 32A2 of which the length of contact with a wavy portion 32B of a second wiring portion 30B is different from that of the first wavy portion 32A1, as wavy portions 32A of a first wiring portion 30A, as illustrated in FIG. 9A.

The fabric material 102 with an electrode wiring includes the first wavy portion 32A1 and the second wavy portion 32A2 of which the period and/or amplitude are different from those of the first wavy portion 32A1, as the wavy portions 32A of the first wiring portion 30A.

In this example, an example in which the length of contact of the second wavy portion 32A2 with the wavy portion 32B of the second wiring portion 30B is shorter than that of the first wavy portion 32A1 is described. In addition, an example in which the period and amplitude of the second wavy portion 32A2 are less than those of the first wavy portion 32A1 is described.

Figure 9B:
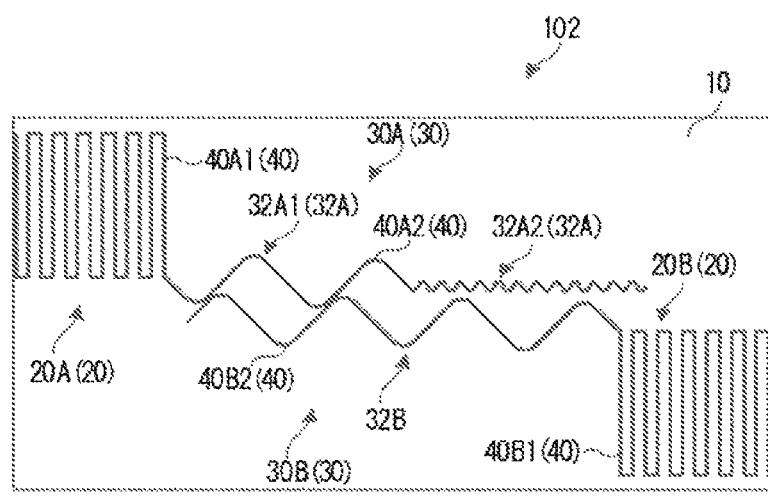
FIG. 9B is a schematic plan view illustrating the first stretched state of the fabric material with an electrode wiring of the second alternative example.

In a case in which the fabric material 102 with an electrode wiring is stretched along the longitudinal direction of the fabric material, a part of the first wiring portion 30A and the second wiring portion 30B, coming into contact with each other, are spaced from each other when a certain stretching rate is reached (see FIG. 9B). Specifically, the second wavy portion 32A2 of the first wiring portion 30A and the wavy portion 32B of the second wiring portion 30B are spaced from each other.

Figure 9C:
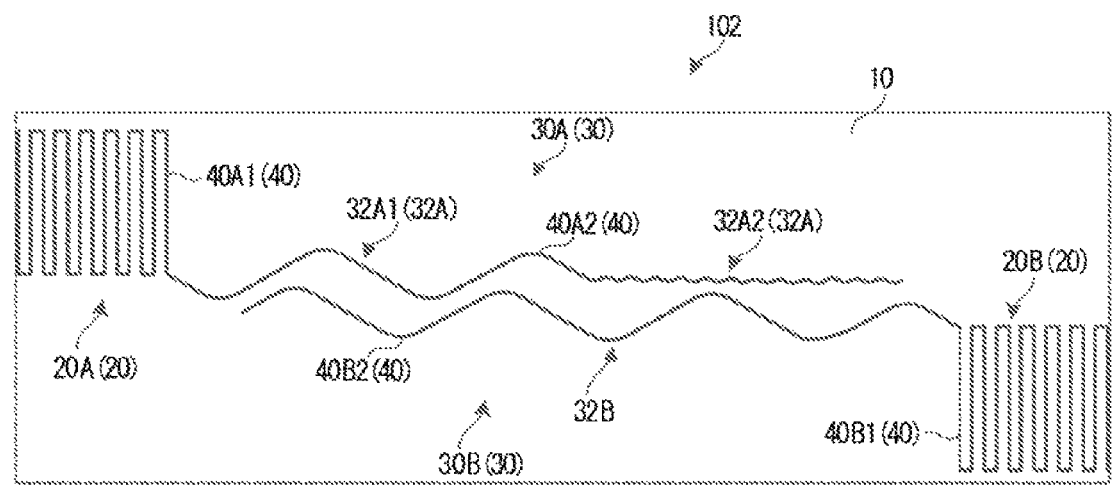
FIG. 9C is a schematic plan view illustrating the second stretched state of the fabric material with an electrode wiring of the second alternative example.

In the case of further performing the stretching, the second wavy portion 32A2 of the first wiring portion 30A and the wavy portion 32B of the second wiring portion 30B are spaced from each other when a certain stretching rate is reached (see FIG. 9C).

In other words, the second wavy portion 32A2 of the first wiring portion 30A and the wavy portion 32B of the second wiring portion 30B are first spaced from each other, and the first wavy portion 32A1 of the first wiring portion 30A and the wavy portion 32B of the second wiring portion 30B are then spaced from each other.

This operation allows a resistance value between a first electrode portion 20A and a second electrode portion 20B to be varied in a stepwise manner in a case in which the fabric material 102 with an electrode wiring is stretched. In other words, the resistance value is increased in a stepwise manner in correspondence to an increase in contact resistance, caused by spacing a part of the first wiring portion 30A and the second wiring portion 30B from each other. Specifically, the resistance value is increased by a certain value in the state of electrical connection between the first electrode portion 20A and the second electrode portion 20B, and the electrical connection is changed to electrical disconnection.

The fabric material 102 with an electrode wiring performs a stepwise switching function by detecting a stepwise variation in the resistance value between the first electrode portion 20A and the second electrode portion 20B, caused by the stretching.

In a case in which the stretching of the fabric material 102 with an electrode wiring is canceled (i.e., the fabric material 102 with an electrode wiring is shrunk), the first wavy portion 32A1 of the first wiring portion 30A and the wavy portion 32B of the second wiring portion 30B, spaced from each other, come into contact with each other when a certain stretching rate is reached (see FIG. 9B). In a case in which the stretching of the fabric material 102 with an electrode wiring is further shrunk, the second wavy portion 32A2 of the first wiring portion 30A and the wavy portion 32B of the second wiring portion 30B, spaced from each other, come into contact with each other when a certain stretching rate is reached (see FIG. 9A). In other words, the resistance value is decreased in a stepwise manner.

Specifically, electrical disconnection between the first electrode portion 20A and the second electrode portion 20B is changed to electrical connection between the first electrode portion 20A and the second electrode portion 20B, and the resistance value is then decreased in the state of the electrical connection.

The fabric material 102 with an electrode wiring also performs a stepwise switching function by detecting a stepwise variation in resistance value between the first electrode portion 20A and the second electrode portion 20B, caused by the shrinking, as described above.

In the second alternative example, a plurality of regions of which the contact lengths are different from each other may be included in the contact portions between the wavy portions 32A of the first wiring portion 30A and the wavy portion 32B of the second wiring portion 30B depending on an intended stepwise variation in resistance value between the first electrode portion 20A and the second electrode portion 20B. At least one of the first wiring portion 30A or the second wiring portion 30B may include a plurality of wavy portions of which the periods and/or amplitudes are different from each other.

A stepwise variation in resistance value (i.e., a stepwise increase or decrease) means that a resistance value is varied, and the resistance value is varied again after the end of the variation in resistance value, in a process of stretching the fabric material with an electrode wiring.

Third Alternative Example

Figure 10A:
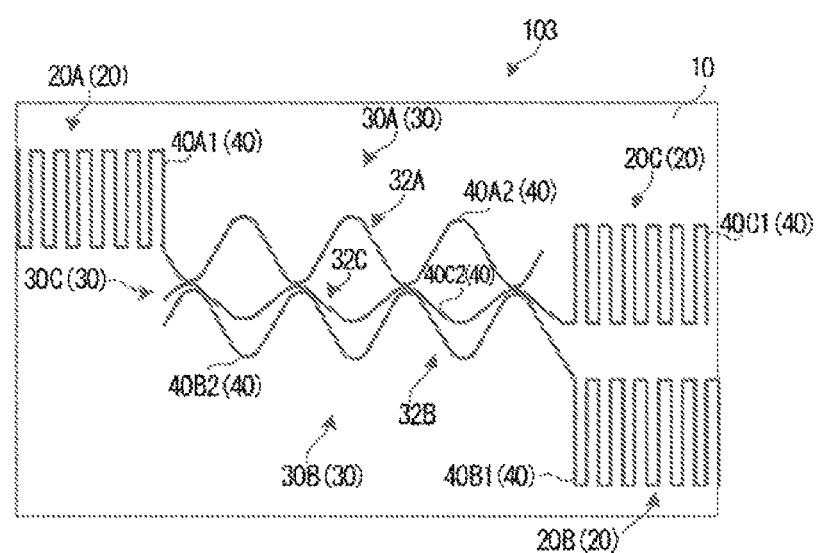
FIG. 10A is a schematic plan view illustrating a fabric material with an electrode wiring of a third alternative example.

The fabric material 100 with an electrode wiring according to the embodiment may be, for example, a fabric material 103 with an electrode wiring illustrated in FIG. 10A. Specifically, the fabric material 103 with an electrode wiring further includes a third electrode portion 20C as an electrode portion 20, and a third wiring portion 30C as a wiring portion 30, as illustrated in FIG. 10A.

The third electrode portion 20C includes a conductive linear body 40C1. The third wiring portion 30C includes a conductive linear body 40C2 formed by extending the conductive linear body 40C1 of the third electrode portion 20C. In other words, the third electrode portion 20C and the third wiring portion 30C include at least one identical conductive linear body 40.

The third electrode portion 20C is directed at one side of a fabric material body 10, in which a second electrode portion 20B exists.

The third wiring portion 30C is electrically connected to the third electrode portion 20C.

The third wiring portion 30C is separate from a first wiring portion 30A and a second wiring portion 30B, exists between the first wiring portion 30A and the second wiring portion 30B, before the fabric material 103 with an electrode wiring is stretched, and is disposed to come into contact with at least a part of the first wiring portion 30A and the second wiring portion 30B.

The third wiring portion 30C also extends, for example, from the third electrode portion 20C toward one side of the fabric material body 10, in which a first electrode portion 20A exists. The third wiring portion 30C also includes at least a wavy portion 32C provided with the conductive linear body 40C2 in wavy form on the central portion of the fabric material body 10.

The wavy portion 32C of the third wiring portion 30C is brought into point contact or line contact with a wavy portion 32A of the first wiring portion 30A and a wavy portion 32B of the second wiring portion 30B before the fabric material 103 with tan electrode wiring is stretched.

However, the length of the contact between the wavy portion 32C of the third wiring portion 30C and the wavy portion 32A of the first wiring portion 30A is different from the length of the contact between the wavy portion 32C of the third wiring portion 30C and the wavy portion 32B of the second wiring portion 30B. The periods and/or amplitudes of the wavy portion 32C of the third wiring portion 30C, the wavy portion 32A of the first wiring portion 30A, and the wavy portion 32B of the second wiring portion 30B are different from each other.

In this example, an example in which the length of the contact between the wavy portion 32C of the third wiring portion 30C and the wavy portion 32A of the first wiring portion 30A is shorter than the length of the contact between the wavy portion 32C of the third wiring portion 30C and the wavy portion 32B of the second wiring portion 30B is described. In addition, an example in which the amplitude of the wavy portion 32C of the third wiring portion 30C is less than those of the wavy portion 32A of the first wiring portion 30A and the wavy portion 32B of the second wiring portion 30B is described.

Figure 10B:
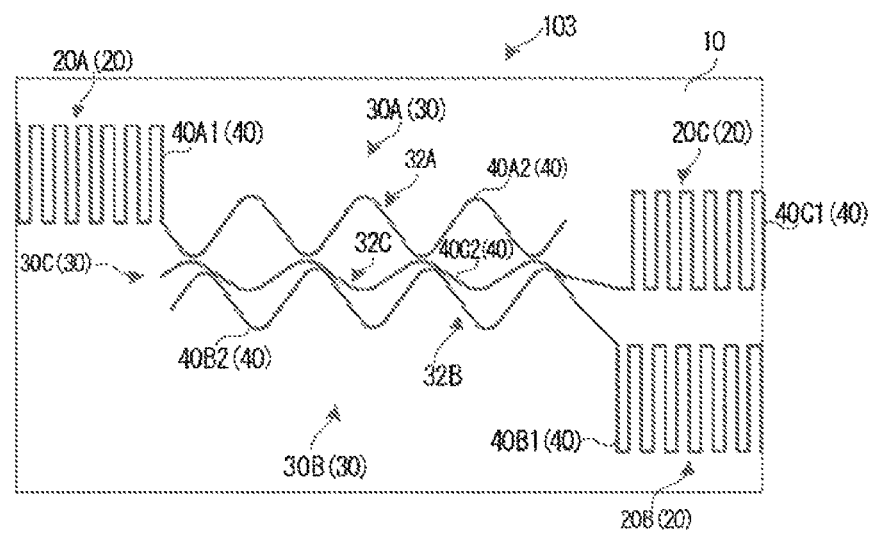
FIG. 10B is a schematic plan view illustrating the first stretched state of the fabric material with an electrode wiring of the third alternative example.

In a case in which the fabric material 103 with an electrode wiring is stretched along the longitudinal direction of the fabric material, the first wiring portion 30A and the third wiring portion 30C, coming into contact with each other, are spaced from each other when a certain stretching rate is reached (see FIG. 10B). Specifically, the wavy portion 32A of the first wiring portion 30A and the wavy portion 32C of the third wiring portion 30C are spaced from each other.

Figure 10C:
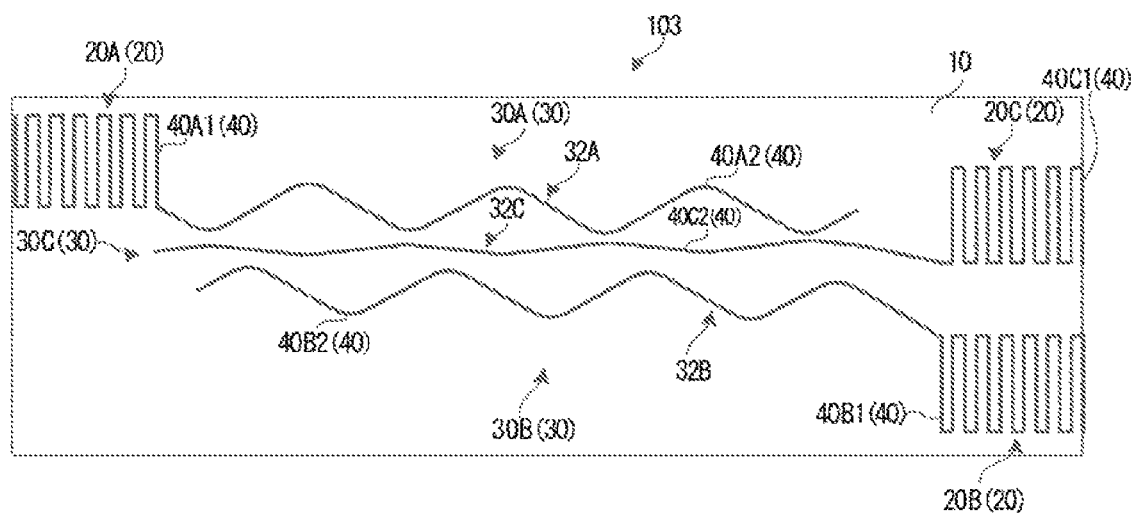
FIG. 10C is a schematic plan view illustrating the second stretched state of the fabric material with an electrode wiring of the third alternative example.

In a case in which the fabric material 103 with an electrode wiring is further stretched, the second wiring portion 30B and the third wiring portion 30C, coming into contact with each other, are spaced from each other when a certain stretching rate is reached (see FIG. 10C). Specifically, the wavy portion 32B of the second wiring portion 30B and the wavy portion 32C of the third wiring portion 30C are spaced from each other.

In other words, the first wiring portion 30A and the third wiring portion 30C are first spaced from each other, and the second wiring portion 30B and the third wiring portion 30C are then spaced from each other.

This operation allows a resistance value between the first electrode portion 20A and the third electrode portion 20C to be varied in a case in which the fabric material 103 with an electrode wiring is stretched. In other words, the resistance value is increased. Specifically, electrical connection between the first electrode portion 20A and the third electrode portion 20C is changed to electrical disconnection between the first electrode portion 20A and the third electrode portion 20C.

A resistance value between the second electrode portion 20B and the third electrode portion 20C is varied in a case in which the fabric material 103 with an electrode wiring is further stretched. In other words, the resistance value is increased. Specifically, electrical connection between the second electrode portion 20B and the third electrode portion 20C is changed to electrical disconnection between the second electrode portion 20B and the third electrode portion 20C.

The fabric material 103 with an electrode wiring performs a stepwise switching function by detecting the variation in resistance value between the first electrode portion 20A and the third electrode portion 20C and the variation in resistance value between the second electrode portion 20B and the third electrode portion 20C, caused by the stretching.

In a case in which the stretching of the fabric material 103 with an electrode wiring is canceled (i.e., the fabric material 103 with an electrode wiring is shrunk), the second wiring portion 30B and the third wiring portion 30C, spaced from each other, come into contact with each other when a certain stretching rate is reached (see FIG. 10B). Specifically, the wavy portion 32B of the second wiring portion 30B and the wavy portion 32C of the third wiring portion 30C come into contact with each other.

In a case in which the fabric material 103 with an electrode wiring is further shrunk, the first wiring portion 30A and the third wiring portion 30C, spaced from each other, come into contact with each other when a certain stretching rate is reached (see FIG. 10A). Specifically, the wavy portion 32A of the first wiring portion 30A and the wavy portion 32C of the third wiring portion 30C come into contact with each other.

In other words, the second wiring portion 30B and the third wiring portion 30C first come into contact with each other, and the first wiring portion 30A and the third wiring portion 30C then come into contact with each other.

The fabric material 103 with an electrode wiring performs a stepwise switching function by detecting a variation in resistance value between the first electrode portion 20A and the third electrode portion 20C and a variation in resistance value between the second electrode portion 20B and the third electrode portion 20C, caused by the shrinking, as described above.

The third alternative example may be an aspect in which the second wiring portion 30B and the third wiring portion 30C are first spaced from each other, and the first wiring portion 30A and the third wiring portion 30C are then spaced from each other.

Fourth Alternative Example

Figure 11A:
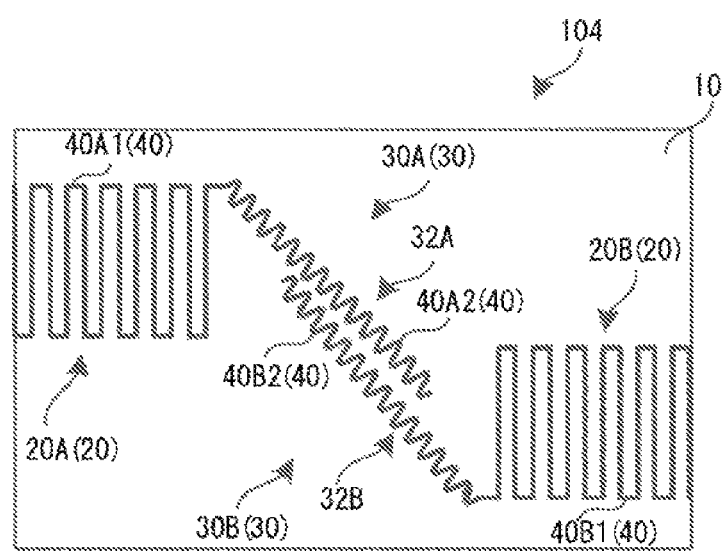
FIG. 11A is a schematic plan view illustrating a fabric material with an electrode wiring of a fourth alternative example.

The fabric material 100 with an electrode wiring according to the embodiment may be, for example, a fabric material 104 with an electrode wiring illustrated in FIG. 11A.

Specifically, the fabric material 104 with an electrode wiring includes a first wiring portion 30A and a second wiring portion 30B, disposed to be spaced from each other before the fabric material 101 with an electrode wiring is stretched, as illustrated in FIG. 11A. A wavy portion 32A of the first wiring portion 30A and a wavy portion 32B of the second wiring portion 30B face each other to form an angle (for example, an angle between the extending directions of the wavy portions of from 3° to 30°), and are disposed to be spaced from each other.

Figure 11B:
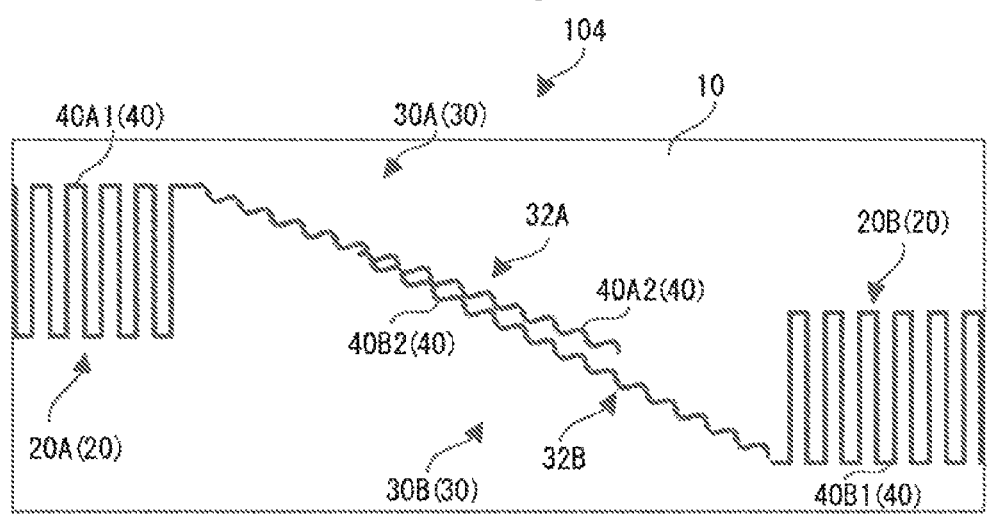
FIG. 11B is a schematic plan view illustrating the first stretched state of the fabric material with an electrode wiring of the fourth alternative example.

In a case in which the fabric material 104 with an electrode wiring is stretched along the longitudinal direction of the fabric material, at least a part of the first wiring portion 30A and the second wiring portion 30B, spaced from each other, come into contact with each other when a certain stretching rate is reached (see FIG. 11B). Specifically, at least a part of a conductive linear body 40A2 included in the first wiring portion 30A and a conductive linear body 40B2 included in the second wiring portion 30B come into contact with each other.

More specifically, in a case in which the fabric material 101 with an electrode wiring is stretched along the longitudinal direction of the fabric material, a leading end of the wavy portion 32B of the second wiring portion 30B (a leading end to which a second electrode portion 40B1 is not connected) approaches and comes into contact with the wavy portion 32A of the first wiring portion 30A while prolonging the periods of the wavy portion 32A of the first wiring portion 30A and the wavy portion 32B of the second wiring portion 30B and decreasing the amplitudes of the wavy portion 32A of the first wiring portion 30A and the wavy portion 32B of the second wiring portion 30B.

Figure 11C:
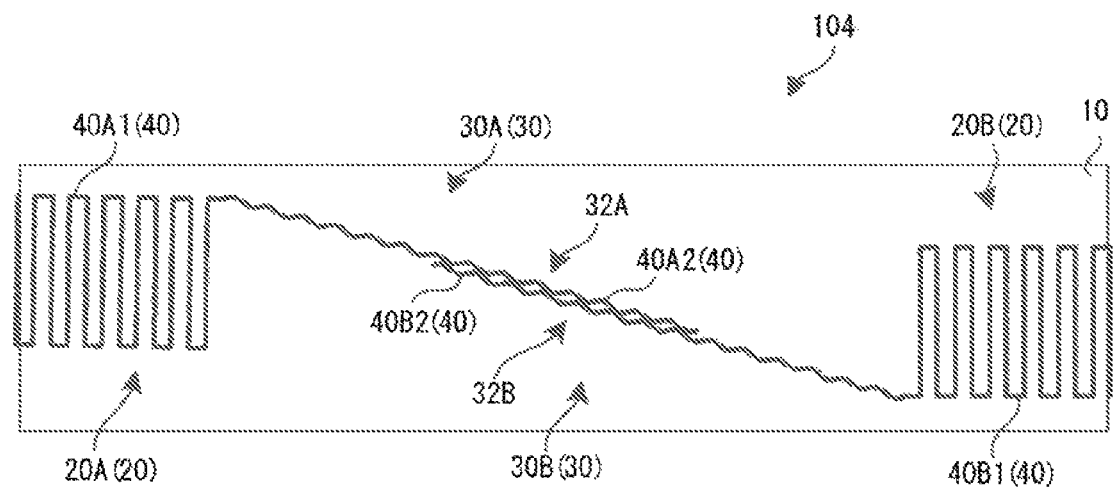
FIG. 11C is a schematic view illustrating the second stretched state of the fabric material with an electrode wiring of the fourth alternative example.

In a case in which the fabric material 104 with an electrode wiring is further stretched, the contact region between the first wiring portion 30A and the second wiring portion 30B is increased (see FIG. 11C). Specifically, the contact region between the conductive linear body 40A2 included in the first wiring portion 30A and the conductive linear body 40B2 included in the second wiring portion 30B is increased.

More specifically, in a case in which the fabric material 104 with an electrode wiring is stretched along the longitudinal direction of the fabric material, the wavy portion 32A of the first wiring portion 30A and the wavy portion 32B of the second wiring portion 30B approach each other to increase the contact region between the wavy portion 32A of the first wiring portion 30A and the wavy portion 32B of the second wiring portion 30B while prolonging the periods of the wavy portion 32A of the first wiring portion 30A and the wavy portion 32B of the second wiring portion 30B and decreasing the amplitudes of the wavy portion 32A of the first wiring portion 30A and the wavy portion 32B of the second wiring portion 30B.

This operation allows a resistance value between a first electrode portion 20A and a second electrode portion 20B to be varied in a stepwise manner in a case in which the fabric material 104 with an electrode wiring is stretched. In other words, electrical disconnection between the first electrode portion 20A and the second electrode portion 20B is changed to electrical connection between the first electrode portion 20A and the second electrode portion 20B in a case in which the first wiring portion 30A and the second wiring portion 30B first come into contact with each other. In a case in which the contact region between the first wiring portion 30A and the second wiring portion 30B is then increased, the contact resistance is decreased, and the resistance value between the first electrode portion 20A and the second electrode portion 20B is decreased in a stepwise manner.

The fabric material 102 with an electrode wiring performs a stepwise switching function by detecting a stepwise variation in resistance value between the first electrode portion 20A and the second electrode portion 20B, caused by the stretching.

In a case in which the stretching of the fabric material 104 with an electrode wiring is canceled (i.e., the fabric material 104 with an electrode wiring is shrunk), the contact region between the first wiring portion 30A and the second wiring portion 30B is decreased (FIG. 11B). In a case in which the fabric material 104 with an electrode wiring is further shrunk, a first wavy portion 32A1 of the first wiring portion 30A and the wavy portion 32B of the second wiring portion 30B, coming into contact with each other, are spaced from each other when a certain stretching rate is reached (see FIG. 11A). In other words, the resistance value is increased in a stepwise manner.

Specifically, the resistance value is decreased in the state of electrical connection between the first electrode portion 20A and the second electrode portion 20B, and the state of the electrical connection is then changed to the state of electrical disconnection between the first electrode portion 20A and the second electrode portion 20B.

The fabric material 104 with an electrode wiring also performs a stepwise switching function by detecting a stepwise variation in resistance value between the first electrode portion 20A and the second electrode portion 20B, caused by the shrinking, as described above.

Fifth Alternative Example

Figure 12A:
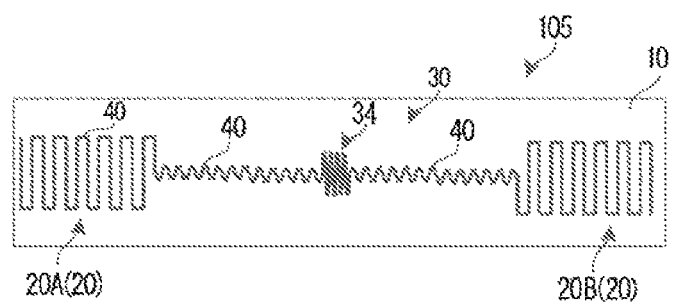
FIG. 12A is a schematic plan view illustrating a fabric material with an electrode wiring of a fifth alternative example.

The fabric material 100 with an electrode wiring according to the embodiment may be, for example, a fabric material 105 with an electrode wiring illustrated in FIG. 12A. Specifically, in the fabric material 105 with an electrode wiring, a first wiring portion 30A and a second wiring portion 30B are integrally disposed as a wiring portion 30, as illustrated in FIG. 12A. Specifically, for example, the first wiring portion 30A and the second wiring portion 30B as the wiring portion 30 include one conductive linear body 40 in which the conductive linear body 40 included in a first electrode portion 20A and a second electrode portion 20B extends.

In other words, in the fabric material 105 with an electrode wiring, the first electrode portion 20A and the second electrode portion 20B are electrically linked by the one wiring portion 30.

The wiring portion 30 may include a plurality of conductive linear bodies 40.

A contact portion 34, in which such wiring portions 30 are repeatedly bent or curved at 180°, and at least a part of the wiring portions 30 in the bent or curved portion come into contact with each other, before the fabric material 105 with an electrode wiring is stretched, is included in the wiring portions 30.

In other words, the contact portion 34, in which such conductive linear bodies 40 are repeatedly bent or curved at 180°, and at least a part of the conductive linear bodies 40 in the bent or curved portion come into contact with each other, before the fabric material 105 with an electrode wiring is stretched, is included in the wiring portions 30.

Figure 12B:
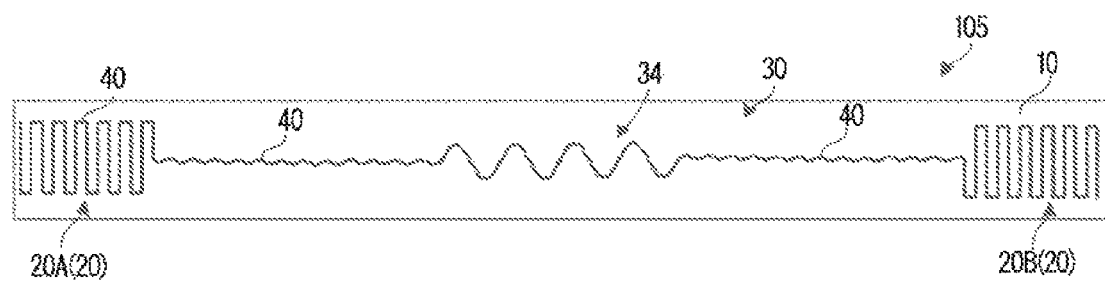
FIG. 12B is a schematic plan view illustrating the stretched state of the fabric material with an electrode wiring of the fifth alternative example.

In a case in which the fabric material 105 with an electrode wiring is stretched along the longitudinal direction of the fabric material (the extending direction of the wiring portions 30), the wiring portions 30 coming into contact with each other in the bent or curved portion are spaced from each other in the contact portion 34 of the wiring portions 30 (see FIG. 12B). As a result, a conduction path between the first electrode portion 20A and the second electrode portion 20B is prolonged.

This operation allows a resistance value between the first electrode portion 20A and the second electrode portion 20B to be varied in a case in which the fabric material 105 with an electrode wiring is stretched. In other words, the resistance value is increased in correspondence to an increase in the conduction path.

The fabric material 105 with an electrode wiring performs a switching function by detecting a variation in resistance value between the first electrode portion 20A and the second electrode portion 20B, caused by the stretching.

In a case in which the stretching of the fabric material 105 with an electrode wiring is canceled (i.e., the fabric material 105 with an electrode wiring is shrunk), the contact portion 34 in which the wiring portions 30 are repeatedly bent or curved at 180°, and at least a part of the wiring portions 30 in the bent or curved portion come into contact with each other is formed in the wiring portions 30 (see FIG. 12A).

This operation allows the resistance value between the first electrode portion 20A and the second electrode portion 20B to be varied in a case in which the fabric material 105 with an electrode wiring is shrunk. In other words, the resistance value is decreased in correspondence to a decrease in the conduction path.

The fabric material 105 with an electrode wiring also performs a switching function by detecting a variation in resistance value between the first electrode portion 20A and the second electrode portion 20B, caused by the shrinking.

In the third alternative example, the amount of variation in resistance value between the first electrode portion 20A and the second electrode portion 20B can be controlled by increasing or decreasing the contact area between the wiring portions 30 in the contact portion of wiring portions 30.

Sixth Alternative Example

Figure 13:
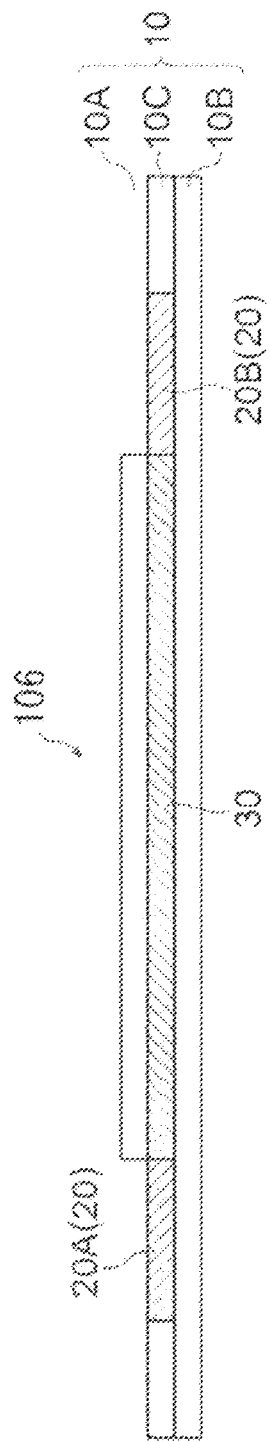
FIG. 13 is a schematic cross-sectional view illustrating the fabric material with an electrode wiring of a sixth alternative example.

The fabric material 100 with an electrode wiring according to the embodiment may be, for example, a fabric material 106 with an electrode wiring, illustrated in FIG. 13. Specifically, the fabric material 105 with an electrode wiring includes a triple fabric material body 10 including a front surface fabric material layer 10A, an intermediate fabric material layer 10C, and a back surface fabric material layer 10B, as illustrated in FIG. 13. Both electrode portions 20 (a first electrode portion 20A and a second electrode portion 20B) and wiring portions 30 (a first wiring portion 30A and a second wiring portion 30B) are disposed in the intermediate fabric material layer 10C.

Specifically, both conductive linear bodies 40A1 and 40B1 included in the electrode portions 20 (the first electrode portion 20A and the second electrode portion 20B), and conductive linear bodies 40A2 and 40B2 included in the wiring portions 30 (the first wiring portion 30A and the second wiring portion 30B) are disposed in the intermediate fabric material layer 10C.

Only the wiring portions 30 disposed in the intermediate fabric material layer 10C are covered with the front surface fabric material layer 10A.

Applications

The fabric material 100 with an electrode wiring according to the embodiment can be utilized in, for example, a stretch sensor for a wearable device, or the like, in order to perform a switching function. In addition, the fabric material 100 with an electrode wiring can also be utilized in a load sensor or the like.

For example, in a case in which the fabric material 100 with an electrode wiring is utilized in a stretch sensor for a wearable device, movement of a moving element such as the elbow or the knee at a predetermined angle can be detected. In addition, the number of times of the movement, and the like can be detected. The sizes of the circumferences of the arm and the waist can also be measured. The detection of movement by multi-measurement is also enabled (for example, the multi-measurement of the arm, the shoulder, the elbow, the knee, the waist, and the like enables the prediction and detection of the movement of a human).

In a case in which the fabric material 100 with an electrode wiring is utilized in a load sensor, application of a predetermined load can be detected. In addition, the number of times of application of a load, and the like can be detected.

In a case in which the fabric material 100 with an electrode wiring is utilized in a stretch sensor for a wearable device, for example, the fabric material 100 with an electrode wiring, equipped with a predetermined instrument may be cut and processed to form clothing with a wearable device. The fabric material 100 with an electrode wiring, cut to have a predetermined size, may also be attached to clothing.

Characteristics

The fabric material 100 with an electrode wiring according to the embodiment preferably has the range of stretching rate, in which the resistance value between the first electrode portion 20A and the second electrode portion 20B is changed to two times or more, or ½ or less (preferably 10 times or more, or ¹⁄₁₀ or less, more preferably 100 times or more, or ¹⁄₁₀₀ or less), in a range of a variation in stretching rate of ±5%, in order to perform a switching function (see FIGS. 6 to 7). In other words, it is preferable that the resistance value between the first electrode portion 20A and the second electrode portion 20B is changed to two times or more, or ½ or less while the stretching rate is varied by 10% in a process in which the fabric material 100 with an electrode wiring is stretched.

Specifically, on the assumption that the maximum stretching rate of the fabric material 100 with an electrode wiring is X (10≤X), and the stretching rate of a certain point in a case in which the fabric material 100 with an electrode wiring is stretched is Y (5≤Y≤(X−5)), it is preferable that a region in which the maximum resistance value is two times or more, or ½ or less (preferably 10 times or more, or ¹⁄₁₀ or less, more preferably 100 times or more, or ¹⁄₁₀₀ or less) of the minimum resistance value is included in a range of from Y−5% to Y+5%.

Such a variation in resistance value is calculated based on the ratio between the resistance values at a time point for which a stretching rate is targeted and at a time point at which the stretching rate at the time point is varied by 10%.

The two or more ranges of the stretching rate, in which the resistance value between the first electrode portion 20A and the second electrode portion 20B is varied to two times or more, or ½ or less in a range of a variation in stretching rate of ±5%, may exist.

It is preferable that the range of the ratio between the stretching rate and the maximum stretching rate (stretching rate/maximum stretching rate), at which the resistance value between the first electrode portion 20A and the second electrode portion 20B is varied to two times or more, or ½ or less in a range of a variation in stretching rate of ±5%, is a range of from 0.1 to 0.9 (preferably from 0.2 to 0.8). In a case in which the ratio is in the range described above, the switching function can be efficiently performed while preventing a malfunction.

A variation in resistance value between the first electrode portion 20A and the second electrode portion 20B, caused by the stretching and shrinking of the fabric material 100 with an electrode wiring, is measured as follows.

While measuring the resistance value between the first electrode portion 20A and the second electrode portion 20B, the fabric material 100 with an electrode wiring is stretched to the maximum stretching at a velocity of 1 mm/s, and then shrunk at the same velocity until the fabric material 100 with an electrode wiring becomes normal again. In such a case, the variation in resistance value is measured while plotting the resistance value every one second. The stretching direction of the fabric material 100 with an electrode wiring is regarded as a direction in which a variation in resistance value, caused by stretching and shrinking, is intended to be detected.

The stretching rate of the fabric material 100 with an electrode wiring is calculated based on Equation: ((length of fabric material in stretching direction in stretching)−(length of fabric material in stretching direction before stretching))/(length of fabric material in stretching direction before stretching)×100.

The maximum stretching rate of the fabric material 100 with an electrode wiring is calculated based on Equation: ((length of fabric material in stretching direction in maximum stretching)−(length of fabric material in stretching direction before stretching))/(length of fabric material in stretching direction before stretching)×100.

The maximum stretching of the fabric material 100 with an electrode wiring refers to the length of the fabric material 100 with an electrode wiring which is no longer stretched in a case in which the fabric material 100 with an electrode wiring is stretched under appropriate tension. In other words, the length of the fabric material 100 with an electrode wiring in a case in which the fabric material 100 with an electrode wiring is stretched under tension allowing the stretching to be stopped is regarded as the maximum stretching of the fabric material 100 with an electrode wiring.

Production Method

A method of producing the fabric material 100 with an electrode wiring according to the embodiment is not particularly limited.

However, from the viewpoint of productivity, it is preferable that the fabric material 100 with an electrode wiring according to the embodiment is produced by the following method.

For example, first, a belt-shaped fabric material 110 in which a plurality of regions in which such fabric materials 100 with electrode wirings exist are formed to be adjacent to each other is produced as illustrated in FIG. 14. The belt-shaped fabric material 110 is formed by forming fabric material bodies 10 by a weaving machine or a knitting machine, and by patterning conductive linear bodies 40 to form each electrode portion 20 and each wiring portion 30. Sites facing each other, in the regions in which the fabric materials 100 with electrode wirings adjacent to each other exist, are formed to be linked to each other by the same conductivity linear body 40.

The plurality of fabric materials 100 with electrode wirings are obtained by cutting the obtained belt-shaped fabric material 110 along predetermined positions (see alternate long and short dash lines C in FIG. 14).

Reference characters are described as follows.
10A Front surface fabric material layer
10B Back surface fabric material layer
10C Intermediate fabric material layer
20 Electrode portion
20A First electrode portion
20B Second electrode portion
20C Third electrode portion
30 Wiring portion
30A First wiring portion
30B Second wiring portion
30C Third wiring portion 32A Wavy portion
32A1 First wavy portion
32A2 Second wavy portion
32B Wavy portion
32C Wavy portion
34 Contact portion
40, 40A1, 40A2, 40B1, 40B2, 40C1, 40C2 Conductive linear body
100, 101, 102, 103, 104, 105, 106 Fabric material with electrode wiring
110 Belt-shaped fabric material The entire disclosure of Japanese Patent Application No. 2018-199111 is incorporated herein by reference.

All the literature, patent application, and technical standards cited herein are also herein incorporated to the same extent as provided for specifically and severally with respect to an individual literature, patent application, and technical standard to the effect that the same should be so incorporated by reference.

The invention claimed is:

1. A fabric material with an electrode wiring, comprising:
a fabric material body with stretchability;
a first electrode portion that is disposed on a surface or in an interior of the fabric material body, and that comprises a conductive linear body;
a first wiring portion that is disposed on the surface or in the interior of the fabric material body so as to be electrically connected to the first electrode portion, and that comprises a conductive linear body with a first pattern;
a second electrode portion that is disposed on the surface or in the interior of the fabric material body, and that comprises a conductive linear body; and
a second wiring portion that is disposed on the surface or in the interior of the fabric material body so as to be electrically connected to the second electrode portion, and that comprises a conductive linear body with a second pattern,
wherein the first electrode portion and the first wiring portion are directly connected to each other,
wherein the second electrode portion and the second wiring portion are directly connected to each other,
wherein the first wiring portion and the second electrode portion are not directly connected to each other, and the second wiring portion and the first electrode portion are not directly connected to each other,
wherein the first and second wiring portions extend side by side between the first electrode portion and the second electrode portion,
wherein the first wiring portion and the second wiring portion are in contact with each other before or after the fabric material is stretched,
wherein when the first wiring portion and the second wiring portion are in contact with each other, there are one or more contacts between the first wiring portion and the second wiring portion, and
wherein a number of the contacts between the first wiring portion and the second wiring portion changes as the fabric material is stretched so that a resistance value between the first electrode portion and the second electrode portion is increased or decreased.

2. The fabric material with an electrode wiring according to claim 1, wherein:
the first wiring portion and the second wiring portion are separately disposed, and
the first wiring portion and the second wiring portion are spaced from each other by stretching the fabric material in a case in which the first wiring portion and the second wiring portion are disposed so that at least a part of the first wiring portion and the second wiring portion come into contact with each other before the fabric material is stretched, or at least a part of the first wiring portion and the second wiring portion are brought into contact with each other by stretching the fabric material in a case in which the first wiring portion and the second wiring portion are disposed to be spaced from each other before the fabric material is stretched.

3. The fabric material with an electrode wiring according to claim 1, wherein:
the first wiring portion and the second wiring portion are separately disposed, and
the number of contacts between the first wiring portion and the second wiring portion is decreased in a stepwise manner and thus a contact region between the first wiring portion and the second wiring portion is decreased in a stepwise manner by stretching the fabric material in a case in which the first wiring portion and the second wiring portion are disposed so that at least a part of the first wiring portion and the second wiring portion come into contact with each other before the fabric material is stretched, or the number of contacts between the first wiring portion and the second wiring portion is increased in a stepwise manner and thus the contact region between the first wiring portion and the second wiring portion is increased in a stepwise manner by stretching the fabric material in a case in which the first wiring portion and the second wiring portion are disposed to be spaced from each other before the fabric material is stretched.

4. The fabric material with an electrode wiring according to claim 1, wherein:
the first wiring portion and the second wiring portion are integrally disposed, and
a conduction path between the first wiring portion and the second wiring portion is prolonged by stretching the fabric material.

5. The fabric material with an electrode wiring according to claim 1, wherein the fabric material has a range of a stretching rate such that the resistance value between the first electrode portion and the second electrode portion is varied by two times or more, in a range of ±5% in which the stretching rate varies, by stretching the fabric material to a maximum stretching rate.

6. The fabric material with an electrode wiring according to claim 1, wherein
the number of contacts between the first wiring portion and the second wiring portion varies in a stepwise manner, and thus the resistance value between the first electrode portion and the second electrode portion varies in a stepwise manner according to a stretching rate of the fabric material.

7. The fabric material with an electrode wiring according to claim 1, wherein
before the fabric material is stretched, a state between the first electrode portion and the second electrode portion is the electrically disconnected state, and when the fabric material is stretched, the state between the first electrode portion and the second electrode portion is changed from the electrically disconnected state to the electrically connected state; or
before the fabric material is stretched, the state between the first electrode portion and the second electrode portion is the electrically connected state, and when the fabric material is stretched, the state between the first electrode portion and the second electrode portion is changed from the electrically connected state to the electrically disconnected state.

8. The fabric material with an electrode wiring according to claim 1, wherein a part of the conductive linear body in at least one of the first electrode portion or the second electrode portion is bound by a yarn of the fabric matelial body.

9. The fabric material with an electrode wiring according to claim 8, wherein the fabric material body is interwoven, woven, or embroidered with the conductive linear body in at least one of the first electrode portion or the second electrode portion.

10. The fabric material with an electrode wiring according to claim 1, wherein a part of the conductive linear body is bound by a yarn of the fabric material body in at least one of the first wiring portion or the second wiring portion.

11. The fabric material with an electrode wiring according to claim 10,
wherein the fabric material body is interwoven, woven, or embroidered with the conductive linear body in at least one of the first wiring portion or the second wiring portion.

12. The fabric material with an electrode wiring according to claim 1, wherein at least one of the first wiring portion or the second wiring portion is disposed in the interior of the fabric material body.

13. The fabric material with an electrode wiring according to claim 1, wherein the conductive linear body contained in at least one of the first electrode portion, the second electrode portion, the first wiring portion, or the second wiring portion is a conductive linear body comprising a carbon nanotube yarn.

14. The fabric material with an electrode wiring according to claim 2, wherein:
the first wiring portion and the second wiring portion are separately disposed, and
the number of contacts between the first wiring portion and the second wiring portion is decreased in a stepwise manner and thus a contact region between the first wiring portion and the second wiring portion is decreased in a stepwise manner by stretching the fabric material in a case in which the first wiring portion and the second wiring portion are disposed so that at least a part of the first wiring portion and the second wiring portion come into contact with each other before the fabric material is stretched, or the number of contacts between the first wiring portion and the second wiring portion is increased in a stepwise manner and thus the contact region between the first wiring portion and the second wiring portion is increased in a stepwise manner by stretching the fabric material in a case in which the first wiring portion and the second wiring portion are disposed to be spaced from each other before the fabric material is stretched.

15. The fabric material with an electrode wiring according to claim 1, wherein the resistance value between the first electrode portion and the second electrode portion is varied by ½ or less, in a range of +5% in which the stretching rate varies, when stretching the fabric material to a maximum stretching rate.

16. The fabric material with an electrode wiring according to claim 1, wherein the contacts between the first wiring portion and the second wiring portion include at least one of point contacts and line contacts.

* * * * *